US005597570A

United States Patent [19]

Sondermeyer et al.

[11] Patent Number: 5,597,570
[45] Date of Patent: Jan. 28, 1997

[54] PROTEIN RECOGNIZED BY ANTIBODIES RAISED AGAINST NATIVE P28 OF SCHISTOSOMA MANSONI

[75] Inventors: Paul Sondermeyer, Strasbourg; Jean-Marc Balloul, Lille; Raymond Pierce, Seclin; Jean-Marie Grzych, Marcq en Baroeul; Marie-Paule Kieny; Gérard Loison, both of Strasbourg; André Capron, Phalempin; Jean-Pierre Lecocq, Reichstett, all of France

[73] Assignee: Transgene S.A., France

[21] Appl. No.: 964,471

[22] Filed: Oct. 21, 1992

Related U.S. Application Data

[63] Continuation of Ser. No. 819,600, Jan. 9, 1992, abandoned, which is a continuation of Ser. No. 663,805, Mar. 4, 1991, abandoned, which is a continuation of Ser. No. 449,449, Dec. 12, 1989, abandoned, which is a continuation of Ser. No. 88,615, Aug. 24, 1987, abandoned.

[30] Foreign Application Priority Data

| Aug. 22, 1986 | [FR] | France | 8611986 |
| Apr. 22, 1987 | [FR] | France | 8705691 |
| Apr. 22, 1987 | [FR] | France | 8705692 |

[51] Int. Cl.$^6$ .......... A61K 39/002; C07K 14/00; C12N 9/10
[52] U.S. Cl. .......... 424/191.1; 530/324; 530/350; 43/193
[58] Field of Search .......... 424/88, 191.1; 530/350, 324; 435/193

[56] References Cited

U.S. PATENT DOCUMENTS

| 4,150,107 | 4/1979 | Enders et al. | 424/9 |
| 4,384,992 | 5/1983 | Capron et al. | 530/300 |
| 4,396,600 | 8/1983 | Messineo et al. | 424/88 |
| 5,051,254 | 9/1991 | Strand | 530/350 |

FOREIGN PATENT DOCUMENTS 0110385   6/1984   European Pat. Off. .

OTHER PUBLICATIONS

Cordingley et al, Molecular and Biochemical Parasitology, 18 (1986) 73–88.
Balloul et al, Molecular and Biochemical Parasitology, 17 (1985) 105–114.
Taylor et al, Chem. Abs. 101, No. 21, 184923.
Aronstein et al, Chem. Abs. Nos. 103, 19, 158710m.
Iino et al, Chem. Abs. 105, No. 13, 1097805.
Knight et al, Chem. Abs. 104, No. 19, 1628629.
Smith et al, Proc. Natl. Acad. Sci. USA (1986) 83 (22), 8703–7 (CA 106(5):28407u).
Davern et al, Immunol. Cell Biol, (1987) 65(6), 473–82, (CA 109 (1), 4955q).
Cordingley et al; Molecular and Biochemical Parasitology, 18 (1986) 73–88; "Identification by Message Selection of cDNA Clones Encoding Antigens of 'Schistosoma Mansoni'".
Balloul et al; Molecular and Biochemical Parasitology, 17 (1985) 105–114; "In Vitro Synthesis of a 28 Kilokalton Antigen Present on the Surface of the Schistosomulum of 'Schistosoma Mansoni'".
J. M. Balloul et al. "Molecular Cloning of a Protective Antigen of Schistosomes" Nature 326:149–153 (Mar. 1987).
Taylor et al. Chem Abs 101, No. 21, 184923 (Nov. 1984).
Aronstein et al. Chem Abs 103, No. 19 158710m (Nov. 1985).
Iino et al. Chem Abs 105 No. 13 109780s (Sep. 1986).
Knight et al. Chem Abs 104 No. 19 162862a (May 1986).
Smith et al., *Proc. Nat'l Aca. Sci* (USA) 1986 83(22), pp. 8703–8707, [CA 106(5): 28407 u].
Davern et al., *Immunol Cell Biol.* (1987), 65(6) pp. 473–482, [CA 109(1), 4955g].
Taylor et al, Chem. Abs. 101, No. 21, 184923 (Nov. 1984).
Aronstein et al, Chem. Abs. 103, No. 19, 158710m (Nov. 1985).
Iino et al, Chem. Abs. 105, No. 13, 1097805 (Sep. 1986).
Knight et al, Chem. Abs. 104, No. 19, 1628629 (May 1986).
Chem. Abs., 101, No. 21, 184923, Taylor et al (Nov. 1984).
Chem. Abs., 103, No. 19, 158710m, Aronstein et al (Nov. 1985).
Chem. Abs. 105, No. 13, 109780s, Iino et al (Sep. 1986).
Chem. Abs. 104, No. 19, 162862a, Knight et al (May 1986).

*Primary Examiner*—Robert A. Wax
*Assistant Examiner*—Rebecca Prouty
*Attorney, Agent, or Firm*—Cushman Darby & Cushman, L.L.P.

[57] ABSTRACT

The present invention relates to the development of a vaccine against schistosomiasis. It relates to a protein which includes the epitopes of the p28 protein, a poxvirus containing a gene coding for the said protein, a cell incorporating a vector for the expression of the said protein, a method for preparing the said protein, a DNA sequence coding for the p28 protein, a pharmaceutical composition, antibodies raised against the said protein and their application by way of diagnostic agents for schistosomiasis.

The present invention also relates to the application of the said protein by way of an agent possessing glutathione S-transferase activity.

4 Claims, 26 Drawing Sheets

TGCAAG                                                    FIG.1a.

7
 ATG GCT GGC GAG CAT ATC AAG GTT ATC TAT
 Met Ala Gly Glu His Ile Lys Val Ile Tyr

37
 TTT GAC GGA CGC GGA CGT GCT GAA TCG ATT
 Phe Asp Gly Arg Gly Arg Ala Glu Ser Ile

67
 CGG ATG ACT CTT GTG GCA GCT GGT GTA GAC
 Arg Met Thr Leu Val Ala Ala Gly Val Asp

97
 TAC GAA GAT GAG AGA ATT AGT TTC CAA GAT
 Tyr Glu Asp Glu Arg Ile Ser Phe Gln Asp

127
 TGG CCA AAA ATC AAA CCA ACT ATT CCA GGC
 Trp Pro Lys Ile Lys Pro Thr Ile Pro Gly

157
 GGA CGA TTG CCT GCA GTG AAA GTC ACT GAT
 Gly Arg Leu Pro Ala Val Lys Val Thr Asp

187
 GAT CAT GGG CAC GTG AAA TGG ATG TTA GAG
 Asp His Gly His Val Lys Trp Met Leu Glu

217
 AGT TTG GCT ATT GCA CGG TAT ATG GCG AAG
 Ser Leu Ala Ile Ala Arg Tyr Met Ala Lys

247
 AAA CAT CAT ATG ATG GGT GAA ACA GAC GAG
 Lys His His Met Met Gly Glu Thr Asp Glu

277
 GAA TAC TAT AGT GTT GAA AAG TTG ATT GGT
 Glu Tyr Tyr Ser Val Glu Lys Leu Ile Gly

307
 CAG GCT GAA GAT GTA GAA CAT GAA TAT CAC
 Gln Ala Glu Asp Val Glu His Glu Tyr His

FIG.1b.

337
AAA ACT TTG ATG AAG CCA CAA GAA GAG AAA
Lys Thr Leu Met Lys Pro Gln Glu Glu Lys

367
GAG AAG ATA ACC AAA GAG ATA TTG AAC GGC
Glu Lys Ile Thr Lys Glu Ile Leu Asn Gly

397
AAA GTT CCA GTT CTT CTC AAT ATG ATC TGC
Lys Val Pro Val Leu Leu Asn Met Ile Cys

427
GAA TCT CTG AAA GGG TCG ACA GGA AAG CTG
Glu Ser Leu Lys Gly Ser Thr Gly Lys Leu

457
GCT GTT GGG GAC AAA GTA ACT CTA GCT GAT
Ala Val Gly Asp Lys Val Thr Leu Ala Asp

487
TTA GTC CTG ATT GCT GTC ATT GAT CAT GTG
Leu Val Leu Ile Ala Val Ile Asp His Val

517
ACT GAT CTG GAT AAA GGA TTT CTA ACT GGC
Thr Asp Leu Asp Lys Gly Phe Leu Thr Gly

547
AAG TAT CCT GAG ATC CAT AAA CAT CGA GAA
Lys Tyr Pro Glu Ile His Lys His Arg Glu

577
AAT CTG TTA GCC AGT TCA CCG CGT TTG GCG
Asn Leu Leu Ala Ser Ser Pro Arg Leu Ala

607
AAA TAT TTA TCG AAC AGG CCT GCA ACT CCC
Lys Tyr Leu Ser Asn Arg Pro Ala Thr Pro

637
TTC TAA ACC TAT CAA CAG AAA GCT CGG TGT
Phe ***

FIG.1c.

667
AAC GAG ATT TAA GAT ATT GAT AGT AAA GGA

697
CTA GTG TCA CCT TTT TAC AAG GAT GTC ATT

727
TGTTTATGGGTGTTTTTTTCGCAATTG 757                                                    787
TTATTAAAATTAACTTAGTTTCCTGTTTAAAAA

FIG. 3a.

NAME OF THE SEQUENCE : (ALP)SM-CIIP28:SEQ

1
| ATG | GTT | CGT | GCA | AAC | AAA | CGC | AAC | GAG | GCT |
|-----|-----|-----|-----|-----|-----|-----|-----|-----|-----|
| Met | Val | Arg | Ala | Asn | Lys | Arg | Asn | Glu | Ala |

31
| CTA | CGA | ATC | GGA | TCC | GAA | TTC | CCC | CCC | CCA |
|-----|-----|-----|-----|-----|-----|-----|-----|-----|-----|
| Leu | Arg | Ile | Gly | Ser | Glu | Phe | Pro | Pro | Pro |

61
| GAT | TGG | CCA | AAA | ATC | AAA | CCA | ACT | ATT | CCA |
|-----|-----|-----|-----|-----|-----|-----|-----|-----|-----|
| Asp | Trp | Pro | Lys | Ile | Lys | Pro | Thr | Ile | Pro |

91
| GGC | GGA | CGA | TTG | CCT | GCA | GTG | AAA | GTC | ACT |
|-----|-----|-----|-----|-----|-----|-----|-----|-----|-----|
| Gly | Gly | Arg | Leu | Pro | Ala | Val | Lys | Val | Thr |

121
| GAT | GAT | CAT | GGG | CAC | GTG | AAA | TGG | ATG | TTA |
|-----|-----|-----|-----|-----|-----|-----|-----|-----|-----|
| Asp | Asp | His | Gly | His | Val | Lys | Trp | Met | Leu |

151
| GAG | AGT | TTG | GCT | ATT | GCA | CGG | TAT | ATG | GCG |
|-----|-----|-----|-----|-----|-----|-----|-----|-----|-----|
| Glu | Ser | Leu | Ala | Ile | Ala | Arg | Tyr | Met | Ala |

181
| AAG | AAA | CAT | CAT | ATG | ATG | GGT | GAA | ACA | GAC |
|-----|-----|-----|-----|-----|-----|-----|-----|-----|-----|
| Lys | Lys | His | His | Met | Met | Gly | Glu | Thr | Asp |

211
| GAG | GAA | TAC | TAT | AGT | GTT | GAA | AAG | TTG | ATT |
|-----|-----|-----|-----|-----|-----|-----|-----|-----|-----|
| Glu | Glu | Tyr | Tyr | Ser | Val | Glu | Lys | Leu | Ile |

241
| GGT | CAG | GCT | GAA | GAT | GTA | GAA | CAT | GAA | TAT |
|-----|-----|-----|-----|-----|-----|-----|-----|-----|-----|
| Gly | Gln | Ala | Glu | Asp | Val | Glu | His | Glu | Tyr |

FIG. 3b.

```
271
    CAC  AAA  ACT  TTG  ATG  AAG  CCA  CAA  GAA  GAG
    His  Lys  Thr  Leu  Met  Lys  Pro  Gln  Glu  Glu

301
    AAA  GAG  AAG  ATA  ACC  AAA  GAG  ATA  TTG  AAC
    Lys  Glu  Lys  Ile  Thr  Lys  Glu  Ile  Leu  Asn

331
    GGC  AAA  GTT  CCA  GTT  CTT  CTC  AAT  ATG  ATC
    Gly  Lys  Val  Pro  Val  Leu  Leu  Asn  Met  Ile

361
    TGC  GAA  TCT  CTG  AAA  GGG  TCG  ACA  GGA  AAG
    Cys  Glu  Ser  Leu  Lys  Gly  Ser  Thr  Gly  Lys

391
    CTG  GCT  GTT  GGG  GAC  AAA  GTA  ACT  CTA  GCT
    Leu  Ala  Val  Gly  Asp  Lys  Val  Thr  Leu  Ala

421
    GAT  TTA  GTC  CTG  ATT  GCT  GTC  ATT  GAT  CAT
    Asp  Leu  Val  Leu  Ile  Ala  Val  Ile  Asp  His 451                                              481
    GTG  ACT  GAT  CTG  GAT  AAA  GGA  TTT  CTA  ACT  GGC
    Val  Thr  Asp  Leu  Asp  Lys  Gly  Phe  Leu  Thr  Gly

511
    AAG  TAT  CCT  GAG  ATC  CAT  AAA  CAT  CGA  GAA  AAT
    Lys  Tyr  Pro  Glu  Ile  His  Lys  His  Arg  Glu  Asn

541
    CTG  TTA  GCC  AGT  TCA  CCG  CGT  TTG       GCG  AAA
    Leu  Leu  Ala  Ser  Ser  Pro  Arg  Leu       Ala  Lys

571
    TAT  TTA  TCG  AAC  AGG  CCT  GCA  ACT  CCC  TTC  TAA
    Tyr  Leu  Ser  Asn  Arg  Pro  Ala  Thr  Pro  Phe  ***
```

FIG.9a.

NAME OF THE SEQUENCE : (ALP)PTG45:SEQ

AGATCTGCAGCA

13
| ATG | TAC | CGC | ATG | CAA | CTC | CTG | TCT | TGT | ATC |
| Met | Tyr | Arg | Met | Gln | Leu | Leu | Ser | Cys | Ile |

43
| GCC | TTA | AGT | CTC | GCA | CTT | GTC | ACA | AAC | AGC |
| Ala | Leu | Ser | Leu | Ala | Leu | Val | Thr | Asn | Ser |

73
| GCT | CCT | ACT | TCA | AGC | TCG | ACA | AAG | GAA | TTC |
| Ala | Pro | Thr | Ser | Ser | Ser | Thr | Lys | Glu | Phe |

103
| CCC | CCC | CCA | GAT | TGG | CCA | AAA | ATC | AAA | CCA |
| Pro | Pro | Pro | Asp | Trp | Pro | Lys | Ile | Lys | Pro |

133
| ACT | ATT | CCA | GGC | GGA | CGA | TTG | CCT | GCA | GTG |
| Thr | Ile | Pro | Gly | Gly | Arg | Leu | Pro | Ala | Val |

163
| AAA | GTC | ACT | GAT | GAT | CAT | GGG | CAC | GTG | AAA |
| Lys | Val | Thr | Asp | Asp | His | Gly | His | Val | Lys |

193
| TGG | ATG | TTA | GAG | AGT | TTG | GCT | ATT | GCA | CGG |
| Trp | Met | Leu | Glu | Ser | Leu | Ala | Ile | Ala | Arg |

223
| TAT | ATG | GCG | AAG | AAA | CAT | CAT | ATG | ATG | GGT |
| Tyr | Met | Ala | Lys | Lys | His | His | Met | Met | Gly |

253
| GAA | ACA | GAC | GAG | GAA | TAC | TAT | AGT | GTT | GAA |
| Glu | Thr | Asp | Glu | Glu | Tyr | Tyr | Ser | Val | Glu |

283
| AAG | TTG | ATT | GGT | CAG | GCT | GAA | GAT | GTA | GAA |
| Lys | Leu | Ile | Gly | Gln | Ala | Glu | Asp | Val | Glu |

FIG. 9b.

```
313
    CAT  GAA  TAT  CAC  AAA  ACT  TTG  ATG  AAG  CCA
    His  Glu  Tyr  His  Lys  Thr  Leu  Met  Lys  Pro

343
    CAA  GAA  GAG  AAA  GAG  AAG  ATA  ACC  AAA  GAG
    Gln  Glu  Glu  Lys  Glu  Lys  Ile  Thr  Lys  Glu

373
    ATA  TTG  AAC  GGC  AAA  GTT  CCA  GTT  CTT  CTC
    Ile  Leu  Asn  Gly  Lys  Val  Pro  Val  Leu  Leu

403
    AAT  ATG  ATC  TGC  GAA  TCT  CTG  AAA  GGG  TCG
    Asn  Met  Ile  Cys  Glu  Ser  Leu  Lys  Gly  Ser

433
    ACA  GGA  AAG  CTG  GCT  GTT  GGG  GAC  AAA  GTA
    Thr  Gly  Lys  Leu  Ala  Val  Gly  Asp  Lys  Val

463
    ACT  CTA  GCT  GAT  TTA  GTC  CTG  ATT  GCT  GTC
    Thr  Leu  Ala  Asp  Leu  Val  Leu  Ile  Ala  Val

493
    ATT  GAT  CAT  GTG  ACT  GAT  CTG  GAT  AAA  GGA
    Ile  Asp  His  Val  Thr  Asp  Leu  Asp  Lys  Gly

523
    TTT  CTA  ACT  GGC  AAG  TAT  CCT  GAG  ATC  CAT
    Phe  Leu  Thr  Gly  Lys  Tyr  Pro  Glu  Ile  His

553
    AAA  CAT  CGA  GAA  AAT  CTG  TTA  GCC  AGT  TCA
    Lys  His  Arg  Glu  Asn  Leu  Leu  Ala  Ser  Ser

583
    CCG  CGT  TTG  GCG  AAA  TAT  TTA  TCG  AAC  AGG
    Pro  Arg  Leu  Ala  Lys  Tyr  Leu  Ser  Asn  Arg

613
            CCT  GCA  ACT  CCC  TTC  TAA
            Pro  Ala  Thr  Pro  Phe  ***
```

FIG. 10a.

NAME OF THE SEQUENCE : (ALP)PTG46:SEQ

AGATCTGCAGCA

```
13
   ATG  TAC  CGC  ATG  CAA  CTC  CTG  TCT  TGT  ATC
   Met  Tyr  Arg  Met  Gln  Leu  Leu  Ser  Cys  Ile

43
   GCC  TTA  AGT  CTC  GCA  CTT  GTC  ACA  AAC  AGC
   Ala  Leu  Ser  Leu  Ala  Leu  Val  Thr  Asn  Ser

73
   GCT  CCT  ACT  TCA  AGC  TCG  ACA  AAG  GAA  TTC
   Ala  Pro  Thr  Ser  Ser  Ser  Thr  Lys  Glu  Phe

103
   CCC  CCC  CCC  CAG  GAA  TAC  TAT  AGT  GTT  GAA
   Pro  Pro  Pro  Gln  Glu  Tyr  Tyr  Ser  Val  Glu

133
   AAG  TTG  ATT  GGT  CAG  GCT  GAA  GAT  GTA  GAA
   Lys  Leu  Ile  Gly  Gln  Ala  Glu  Asp  Val  Glu

163
   CAT  GAA  TAT  CAC  AAA  ACT  TTG  ATG  AAG  CCA
   His  Glu  Tyr  His  Lys  Thr  Leu  Met  Lys  Pro

193
   CAA  GAA  GAG  AAA  GAG  AAG  ATA  ACC  AAA  GAG
   Gln  Glu  Glu  Lys  Glu  Lys  Ile  Thr  Lys  Glu

223
   ATA  TTG  AAC  GGC  AAA  GTT  CCA  GTT  CTT  CTC
   Ile  Leu  Asn  Gly  Lys  Val  Pro  Val  Leu  Leu

253
   AAT  ATG  ATC  TGC  GAA  TCT  CTG  AAA  GGG  TCG
   Asn  Met  Ile  Cys  Glu  Ser  Leu  Lys  Gly  Ser

283
   ACA  GGA  AAG  CTG  GCT  GTT  GGG  GAC  AAA  GTA
   Thr  Gly  Lys  Leu  Ala  Val  Gly  Asp  Lys  Val
```

FIG.10b.

```
313
    ACT  CTA  GCT  GAT  TTA  GTC  CTG  ATT  GCT  GTC
    Thr  Leu  Ala  Asp  Leu  Val  Leu  Ile  Ala  Val

343
    ATT  GAT  CAT  GTG  ACT  GAT  CTG  GAT  AAA  GGA
    Ile  Asp  His  Val  Thr  Asp  Leu  Asp  Lys  Gly

373
    TTT  CTA  ACT  GGC  AAG  TAT  CCT  GAG  ATC  CAT
    Phe  Leu  Thr  Gly  Lys  Tyr  Pro  Glu  Ile  His

403
    AAA  CAT  CGA  GAA  AAT  CTG  TTA  GCC  AGT  TCA
    Lys  His  Arg  Glu  Asn  Leu  Leu  Ala  Ser  Ser

433
    CCG  CGG  GGG  GGG  GGG  GGA  ATT  CTG  TGA
    Pro  Arg  Gly  Gly  Gly  Gly  Ile  Leu  ***
```

FIG. 16a.

```
1                                   31
GAATTCCCCCCCCCCCCCATCGTGGCATGGCTCCTTACAGAA
   GluPheProProProProIleValAlaTrpLeuLeuThrGlu
    AsnSerProProProProSerTrpHisGlySerLeuGln
    IleProProProProHisArgGlyMetAlaProTyrArg

61
    TTGTGTTTATTCGCCATGCAGAGAGTGTTTACAAIG
     LeuCysLeuPheAlaMetGlnArgValPheThrMet
     AsnCysValTyrSerProCysArgGluCysLeuGln***
     IleValPheIleArgHisAlaGluSerValTyrAsnGlu

91
 AAGAAAATCGATTTTGTGGTTGGCATGATGCAGATCTTTCAG
    LysLysIleAspPheValValGlyMetMetGlnIlePheGln
    ArgLysSerIleLeuTrpLeuAla***CysArgSerPheArg
    GluAsnArgPheCysGlyTrpHisAspAlaAspLeuSerGln 121                                 151
   GACAAGGTATCACTGAGGCTAAACAAGCTGGCCAACTTCTAC
     AspLysValSerLeuArgLeuAsnLysLeuAlaAsnPheTyr
     ThrArgTyrHis***Gly***ThrSerTrpProThrSerThr
     GlnGlyIleThrGluAlaLysGlnAlaGlyGlnLeuLeu

181
    GCCAAAATCACTTCACCTTTGATATTGCCTATACAAGCG
     AlaLysIleThrSerProLeuIleLeuProIleGlnAla
     ProLysSerLeuHisLeu***TyrCysLeuTyrLys
     ArgGlnAsnHisPheThrPheAspIleAlaTyrThrSer

211
    TTCTAAAAGAGCCATCAAGACTTTAAACTTTGTCCTTG
     Phe***LysGluProSerArgLeu***ThrLeuSerLeu
     ArgSerLysLysSerHisGlnAspPheLysLeuCysPro***
     ValLeuLysArgAlaIleLysThrLeuAsnPheValLeuAsp 241                                 271
  ATGAACTTGATCTTAACTGGATACCTGTGACAAAAACATGGC
    MetAsnLeuIleLeuThrGlyTyrLeu***GlnLysHisGly
    *Thr*Ser***LeuAspThrCysAspLysAsnMet
    GluLeuAspLeuAsnTrpIleProValThrLysThrTrp
```

FIG. 16b.

```
301
GTCTAAATGAAAGAATGTACGGTGCTCTTCAAGGTCTG
  Val***MetLysGluCysThrValLeuPheLysVal***
   AlaSerLys***LysAsnValArgCysSerSerArgSer
   ArgLeuAsnGluArgMetTyrGlyAlaLeuGlnGlyLeu

331
AATAAGTCTGAAACTGCTGCCAAACATGGAGAGGAACAAG
   IleSerLeuLysLeuLeuProAsnMetGluArgAsnLys
   Glu***Val***AsnCysCysGlnThrTrpArgGlyThrSer
   AsnLysSerGluThrAlaAlaLysHisGlyGluGluGlnVal 361                              391
TTAAAATATGGAGACGTGCTTATGATATACCTCCCCCTCCTG
   LeuLysTyrGlyAspValLeuMetIleTyrLeuProLeuLeu
   *AsnMetGluThrCysLeu*TyrThrSerProSerCys
   LysIleTrpArgArgAlaTyrAspIleProProProProVal

421
TTGACATTTCAGATCCTCGCTTCCCCGGTAATGAACCAA
   LeuThrPheGlnIleLeuAlaSerProValMetAsnGln
   *HisPheArgSerSerLeuProArg****Thr
   AspIleSerAspProArgPheProGlyAsnGluPro

451
AGTATGCCTTACTTGACTCTTCCTGCATACCACGTACTG
   SerMetProTyrLeuThrLeuProAlaTyrHisValLeu
   LysValCysLeuThr***LeuPheLeuHisThrThrTyr***
   LysTyrAlaLeuLeuAspSerSerCysIleProArgThrGlu 481                              511
AGTGTTTAAAGGACACTGTTCAACGTGTACTGCCATTTTGGTTT
   SerVal***ArgThrLeuPheAsnValTyrCysHisPheGlyLeu
   ValPheLysGlyHisCysSerThrCysThrAlaIleLeuVal
   CysLeuLysAspThrValGlnArgValLeuProPheTrpPhe

541
GATACTATTTCTGCAAGTATAAAGAGACGCGAACAGGTTCT
   IleLeuPheLeuGlnVal***ArgAspAlaAsnArgPhe*
   ***TyrTyrPheCysLysTyrLysGluThrArgThrGlySer
   AspThrIleSerAlaSerIleLysArgArgGluGlnValLeu
```

FIG. 16c.

571
GATTGTCGCCCATGGAAACAGTTTAAGAGCGCTTA
\*\*LeuSerProMetGluThrVal\*\*\*GluArgLeu
AspCysArgProTrpLysGlnPheLysSerAlaTyr
IleValAlaHisGlyAsnSerLeuArgAlaLeuIle

FIG. 16d.

601                                                              631
TCAAGTACTTGGATAATACATCTGATTCAGATATTGTGGACTCAA
SerSerThrTrpIleIleHisLeuIleGlnIleLeuTrpThrGln
GlnValLeuGly*TyrIle*PheArgTyrCysGlyLeu
LysTyrLeuAspAsnThrSerAspSerAspIleValAspSer

661
TATACCCACTGGTATTCCACTAGTCTATGAAC
TyrThrHisTrpTyrSerThrSerLeu***
AsnIleProThrGlyIleProLeuValTyrGlu
IleTyrProLeuValPheHis***SerMetAsn

691
TGGATGCGAACTTGAAGCCAACCAAACACTATTATCTTGCCGA
ThrGlyCysGluLeuGluAlaAsnGlnThrLeuLeuSerCysArg
LeuAspAlaAsnLeuLysProThrLysHisTyrTyrLeuAlaAsp
TrpMetArgThr***SerGlnProAsnThrIleIleLeuProMet 721                                                              751
TGAAGCGACAGTAGCAGCAGCAATAGCACGTGTGGCGAACCAGGG
***SerAspSerSerSerSerAsnSerThrCysGlyGluProGly
GluAlaThrValAlaAlaAlaIleAlaArgValAlaAsnGln
LysArgGln*GlnGlnGln*HisValTrpArgThrArg

781
AAAAAAGAAATGAAGCGAATAATTATCATT
LysLysGluMetLysArgIleIleIleIle
GlyLysLysLys*SerGlu*LeuSerLeu
GluLysArgAsnGluAlaAsnAsnTyrHis

811
ATCGATAATTTCTTCATTATTCATCCATCCATTTAACACATGTTT
IleAspAsnPhePheIleIleHisProSerIle***HisMetPhe
SerIleIleSerSerLeuPheIleHisProPheAsnThrCysPhe
TyrArg***PheLeuHisTyrSerSerIleHisLeuThrHisValLeu 841                                                              871
TGAATAATTTTAGTTCATCTATAGCTTTGAGTAATGAACAGATAC
*IleIleLeuValHisLeu*Leu***ValMetAsnArgTyr
Glu*Phe*PheIleTyrSerPheGlu******ThrAsp
AsnAsnPheSerSerSerIleAlaLeuSerAsnGluGln

FIG. 16e.

901
TGATCGTCCTTACTCATAATCGTATTGTATGAG
***SerSerLeuLeuIleIleValLeuTyrGlu
ThrAspArgProTyrSer***SerTyrCysMetSer
IleLeuIleValLeuThrHisAsnArgIleVal***Val

931
TAATATTTGCCTTAAAAAAAAA
*TyrLeuPro*LysLys
AsnIleCysLeuLysLysLys
IlePheAlaLeuLysLysLys

PROTEIN RECOGNIZED BY ANTIBODIES RAISED AGAINST NATIVE P28 OF SCHISTOSOMA MANSONI

This is a continuation of application No. 07/819,600, filed Jan. 9, 1992, which was abandoned upon the filing hereof which is a continuation of 07/663,805, filed Mar. 4, 1991, now abandoned; which is a continuation of 07/449,449 filed Dec. 12, 1989; now abandoned; which is a continuation of 07/088,615, filed Aug. 24, 1987, now abandoned.

The present invention relates to the development of a vaccine against schistosomiasis.

Schistosomiasis (or bilharziasis) is a parasitic disease of the tropical and subtropical regions of the whole world (except for North America): it is even spreading in North Africa; there is a substantial source of it in Egypt and attention has been drawn to a few sources in Spain and Portugal.

This disease affects from 200 to 400 million human beings. The parasite responsible, the schistosome, is a small flatworm whose complex life cycle involves an intermediate host which is a freshwater mollusc. For this reason, the disease is spreading with the creation of dams and irrigation networks designed for the purpose of developing the tropical areas.

Five types of schistosomes which are pathogenic for man are known: the most widespread, *S. mansoni,* is common to Africa and America; two species, *S. haematobium* and *intercalatum,* are found only in Africa, and two others, *S. japonicum* and *mekongi,* in Asia.

Knowledge of the life cycle of the parasite is necessary for the development of a strategy for preventing the disease.

In effect, the parasite shows an almost perfect adaptation to the host's natural defenses: when it reaches the adult stage, it completely eludes the immune mechanisms and may live for 5 to 20 years in the blood vessels close to the intestinal wall or to the bladder, depending on the species (*S. mansoni* or *S. haematobium,* respectively). The parasite does not multiply in man but the female lays up to 3,000 eggs per day. These eggs and the waste products of the worm's metabolism appear in the host's circulation and produce various disorders (intestinal and urinary disorders, weakness, anemia, granuloma formation with obstruction of the capillary blood vessels leading to tissue fibrosis and, in particular, to serious liver inflammation).

The eggs, provided with a spur, can pass through the intestinal or bladder wall where they produce microlesions, and they are then eliminated. If they rapidly make contact with water, they release ciliated larvae (miracidia) therein, which swim until they penetrate a mollusc. In this intermediate host, the larva engages in cycles of asexual multiplication which will give rise to cercariae which will be released into the water. (A mollusc infected by a single miracidium can produce more than 50,000 cercariae in a Life span of 8 to 10 months).

The cercaria is a swimming larva which lives for only 1 to 2 days. When it encounters a mammal, especially man, it penetrates through the latter's skin. In the skin, it is converted to a *schistosomulum,* an immature form of the parasite, which will be carried in the blood circulation, successively to the heart, the lungs and finally the liver. It is in the hepatic circulation that the parasite becomes adult. The male and the female mate; the female lodges in a canal formed by the infolding of the male's body, and the pair settles permanently in an abdominal blood vessel where the female begins laying eggs.

The complete maturation of the schistosomulum to adult worm takes about 15 days. At the adult stage, the parasite has adsorbed molecules of its host at its surface and, by virtue of this camouflage, it eludes the host's immune recognition and defense mechanisms. In addition, the parasite secretes substances which have an immuno-suppressant capacity. Thus protected, each pair of schistosomes can live in its host for many years while laying thousands of eggs each day.

A drug exists which is effective against the adult parasite, namely praziquantel, but it is too expensive for its widespread use to be envisaged in developing countries. Furthermore, it does not prevent reinfection; in point of fact, in endemically infected areas, the populations are in regular contact with water contaminated with the larvae.

The only serious hope of preventing the disease lies in developing an effective vaccine against the immature form of the parasite, the schistosomulum. This vaccine should be administered to young children so as to avoid the primary infection, and to already contaminated individuals after a treatment with praziquantel to prevent reinfection.

This vaccine should contain one (or more) major antigen(s) of the schistosomulum and induce an effective immune reaction against the larva before the latter eludes the host's defense mechanisms.

Recent work (see review by Capron and Dessaint-1985) has made it possible to identify a limited number of protein antigens present at the surface of the parasite and its larva, and which might play an important part in the induction of an immune response.

One of these antigens has been demonstrated by Balloul et al. (1985): after immunization of rats with extracts of *S. mansoni* purified on gel, the induced antibodies recognize a 28-kd antigen, referred to as p28, which is present on the adult and larval forms of the parasite. These same antibodies recognize a product of in vitro translation of the mRNAs extracted from the adult parasite and one of the external proteins of the schistosomulum, the protein being identified by labeling with $^{125}$I.

Although they cannot by themselves neutralize the schistosomulum, these anti-p28 antibodies activate the cytotoxic cellular response which can kill the schistosomula.

Rats and mice were inoculated with a sample of the purified p28 protein; the immunized animals developed a high degree of protection against an experimental infection with the schistosomula (Balloul et al. 1986).

This set of observations demonstrates the importance of the p28 antigen in the induction of a protective immune response.

The present invention relates to the identification and determination of the cDNA sequence which codes for the p28 antigen, or at least for a polypeptide which includes the epitopes of p28 which are recognized by antibodies raised against the native p28 protein.

Thus, the present invention relates, in the first place, to the DNA sequence coding for the mature p28 protein as depicted in FIG. 1a–1c.

The present invention also relates to the protein whose synthesis is directed by this cDNA, a synthesis which can be accomplished in different host cells, bacteria, yeasts or higher cells, depending on the vector into which the cDNA is inserted and the signals for control of the expression under which it is placed.

The protein according to the present invention can have a primary structure identical to that of the native p28 protein present in the *schistosomulum,* but it can also be a derivative of the latter or a p28 protein which is incomplete but includes the epitopes that are important for recognition by the antibodies and hence for induction of the immunity. This protein or the incomplete protein can also be fused to another protein (or protein fragment) as a result of a genetic manipulation of the corresponding DNA segments which is designed to favor improved expression of the protein in the host cell or, where appropriate, to cause it to be excreted out of the cell.

The technologies by means of which a foreign gene may be cloned and expressed in different host cells are known to those versed in the art. They will be illustrated in the examples below, it being understood that other vectors and other host cells may be used.

The expression of the gene corresponding to p28 in a bacterium, specifically *E. coli*, was obtained with a vector which includes the lambda $P_L$ promoter and the cII rbs as ribosome binding site. The hybrid protein obtained contains a portion of the cII protein, and the p28 protein or a portion of the latter.

In the case where the host is a yeast, for example *S. cerevisiae*, it is possible to use a plasmid vector for yeast containing a functional origin of replication in yeast, for example the origin of replication of the 2μ plasmid, and a selection gene such as URA3. In the present case, the promoter used is that of the PGK gene with the 5' portion of the PGK gene which leads either to a fused protein or to a mature protein.

Finally, when the host is a mammalian cell, a poxvirus, for example vaccinia virus, in which the gene coding for the protein will be placed under the control of a sequence for expression of this gene by the poxvirus, will preferably be used as an expression vector. This recombinant virus will contain the gene coding for a protein according to the invention, preferably inserted in the TK gene of the vaccinia and under the control of a strong promoter such as the 7.5 K protein promoter of the vaccinia. The gene coding for the protein according to the invention may also be fused to a region coding for a functional signal sequence, for example the signal sequence for interleukin-2 or for the rabies glycoprotein, in order to provide for the excretion of the protein out of the cell; in this case the corresponding protein will be a hybrid protein containing a protein portion not originating from the *schistosomula*.

The gene coding for the protein according to the invention may also be fused to a region coding for the transmembrane region of the rabies virus glycoprotein, in order to provide for anchoring of the protein in the cytoplasmic membrane of the infected cells.

The invention also relates to the host cells transformed by the vectors for expression of the proteins according to the present invention, as well as to a method for preparing such proteins, wherein these host cells are cultured and wherein the proteins according to the invention are recovered.

The culture methods and those of recovery and separation of the proteins will obviously depend on the host, but are known to those versed in the art.

Finally, the present invention relates to the pharmaceutical compositions which are useful as vaccines against schistosomiasis, which vaccines contain at least one protein or one poxvirus according to the invention, in a pharmaceutically acceptable vehicle.

The present invention relates especially to live vaccines, which contain live recombinant vaccinia viruses that express the protein according to the invention and which are presented in a pharmaceutically acceptable vehicle.

Preferably, these vaccines will be in a form that may be administered, for example, by injection. The pharmaceutically acceptable vehicle may be an aqueous vehicle for injection.

The vaccination process will have to be appropriate to the type of vaccine used (protein or live virus).

Finally, the present invention relates to the antisera raised against a protein according to the present invention.

The present invention relates, in addition, to the demonstration that the recombinant p28 protein (or p28I) has glutathione S-transferase enzyme activity.

Glutathione S-transferases are very widely distributed enzymes which are present in both plants and animals and which play a part in the detoxification of various molecules (hydrophobic electrophilic compounds, endogenous superoxides, alkylating agents, herbicides, etc.).

The work of Smith et al. (1986) shows that the parasite *Schistosoma japonicum* synthesizes a glutathione S-transferase which might play a part in protecting the parasite against the free radicals produced by the cells which are the effectors of the infected host's immunity.

The present invention relates more especially to the demonstration that the p28 protein derived from *Schistosoma mansoni* and synthesized in *E. coli* or *S. cerevisiae*, and whose value as a vaccinal antigen has been shown above, has glutathione S-transferase activity.

More especially, the present invention relates to the application of a protein as described above by way of an agent possessing glutathione S-transferase activity, such as the p28 protein.

The present invention also relates to the application of the cells, transformed or infected with a block for expression of the protein described above, by way of an agent possessing glutathione S-transferase activity.

These proteins and these cells can be used as a conversion agent in a microbiological conversion process employing glutathione S-transferase activity.

The present invention encompasses the identification and determination of the cDNA sequence which codes for a second p28 protein recognized by the antibodies raised against the native p28 protein.

The present invention relates, in effect, to the DNA sequence coding for the mature p28II protein as depicted in FIG. 16a–16e.

The present invention also relates to a protein whose synthesis is directed by this cDNA or a portion of this cDNA, the said protein being recognized by the antibodies raised against the native p28 protein.

The present invention also relates to the cells which incorporate cDNA coding for the mature p28II protein or a fragment of the latter as described above.

Although in the examples below the protein is expressed only in a bacterium, *E. coli*, its synthesis may also be accomplished in different host cells, bacteria, yeasts or higher cells, depending on the vector into which the cDNA is inserted, as has been described above.

The expression of the gene corresponding to p28II was obtained with the vector described above, which includes the lambda $P_L$ promoter and the cII rbs ribosome binding site.

The present invention also relates to the preparation of the said proteins by culturing the cells described above.

Finally, the invention relates to the pharmaceutical composition for the treatment or prevention of schistosomiasis, which contains by way of active agent at least one protein as described above.

Naturally, if the cDNA is incorporated in a poxvirus such as vaccinia, this poxvirus may, in some cases, be used directly as a vaccinating agent.

It is also possible to raise antibodies against these proteins. These antibodies and these proteins may be used as a diagnostic agent for schistosomiasis.

In the present invention, the nucleotide sequences of the genes or amino acid sequences of the proteins which are shown in the figures are not restated, but are an integral part of the invention and of the present description.

The examples below are designed to demonstrate other characteristics and advantages of the present invention.

The description will be given using the attached figures.

The attached figures are as follows:

FIGS. 1a–1c show the complete sequence of the cDNA deduced from the sequences of λ TG06, λ TG08, λ TG09, λ TG10 and λ TG11.

The open reading-frame which begins at the 7th nucleotide codes for a polypeptide of 211 amino acids having a molecular weight of 28 kd.

FIGS. 3a and 3b show the sequence of the cII/p28 fusion protein encoded by the expression block inserted into pTG44.

The arrow shows the position of the 25-kd protein.

A. total extract of TGE901 pTG44 at 30 ° C.
B. insoluble fraction of the same extract
C. total extract of TGE901 pTG44 after induction for 7 hours at 37° C.
D. insoluble fraction of the same extract
E. total extract of TGE901 pTG44 after induction for 7 hours at 42° C.
F. insoluble fraction of the same extract
G. fraction F. solubilized in 0.2% SDS
H. total extract of control culture of TGE901 pTG1924 after 7 hours at 42° C.
I. insoluble fraction of the same extract.

Figure 5:
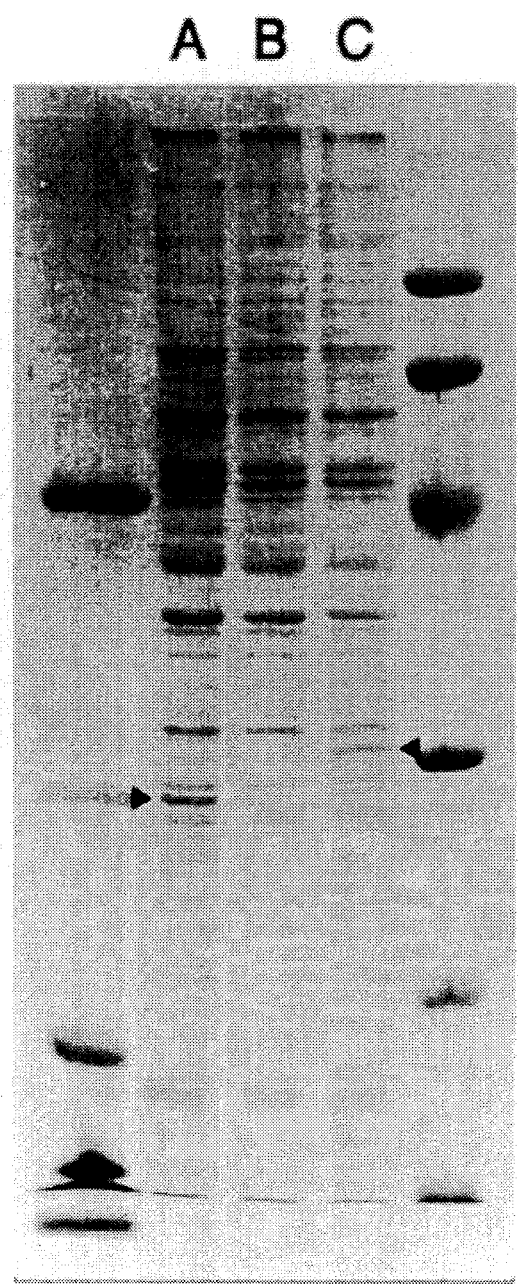

FIG. 5 shows extracts of S. cerevisiae TGY1sp4 producing the p28 protein encoded by the constructions pTG1885 and pTG1886, after electrophoresis on SDS-acrylamide gel and staining with Coomassie blue.

A. extract of TGY1sp4/pTG1885 (non-fused 28-kd protein)
B. extract of TGY1sp4 control culture
C. extract of TGY1sp4/pTG1886 (fused 30-kd protein).

Figure 6:
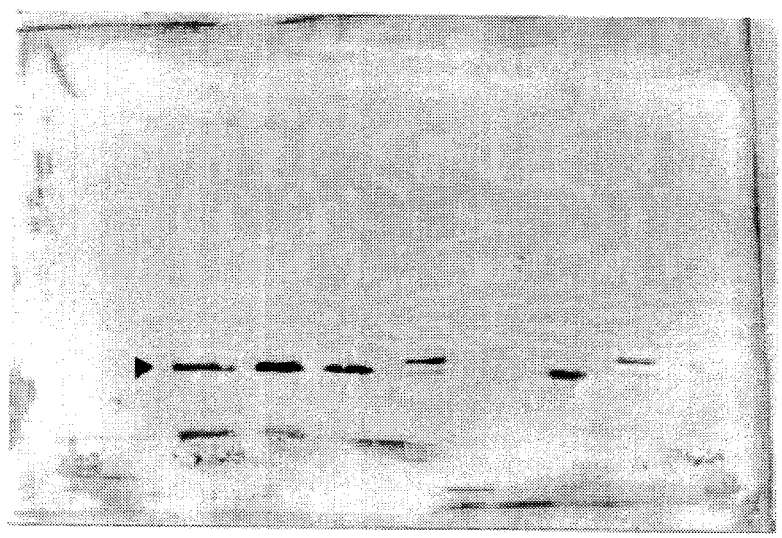

FIG. 6 shows extracts of E. coli and S. cerevisiae producing a fused or mature 28-kd protein, the extracts being analyzed by "Western blotting" with rabbit antibodies specific for the native p28. The bound antibodies are recognized by biotin-labeled anti-rabbit antibodies and this complex is then visualized by means of a streptavidin-peroxidase reagent and staining with HRP (Bio-Rad).

A. total extract of coli TGE901 pTG44
B. insoluble fraction of the same extract
C. total extract of S. cerevisiae, TGY1sp4/pTG1885, producing the mature protein
D. total extract of S. cerevisiae producing the mature protein fused to the first 22 amino acids of PGK, TGY1sp4/pTG1886
E. extract of negative control S. cerevisiae
F.,G. same extracts as C and D, at half the concentration.

Figure 7:
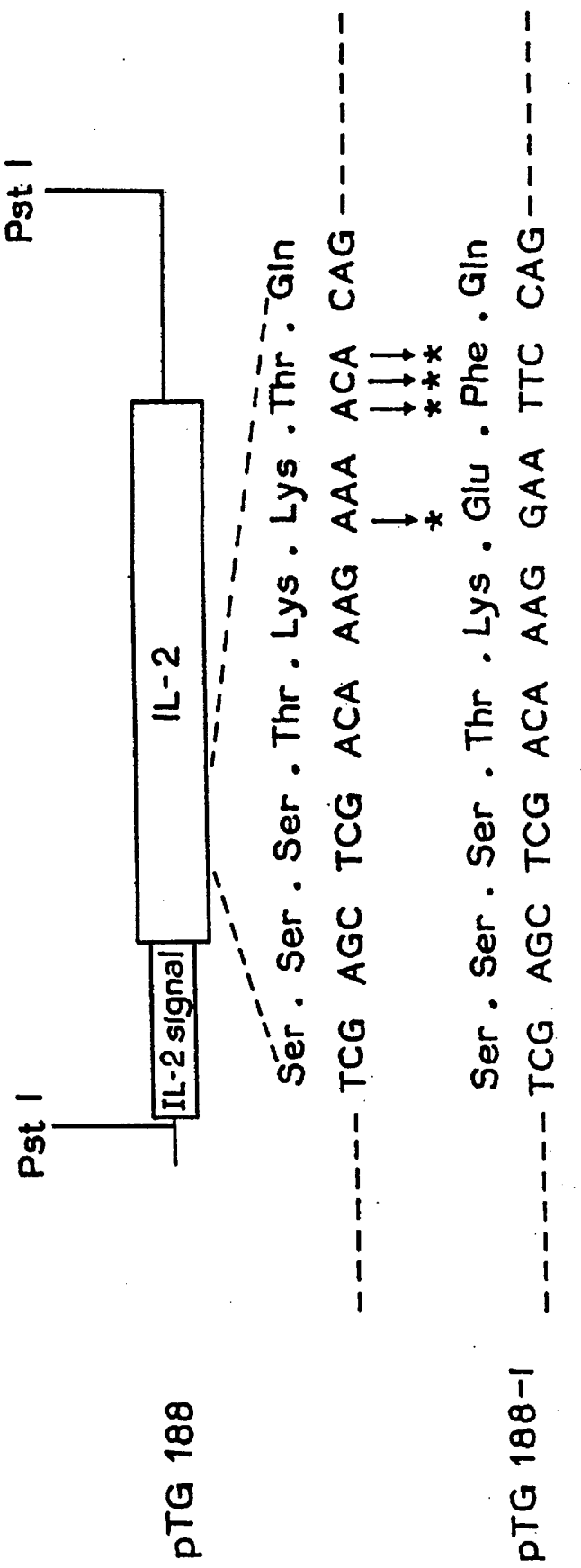

FIG. 7 shows the placing in phase of the EcoRI site by directed mutagenesis in the region of the cDNA corresponding to the first 9 amino acids of human interleukin-2.

Figure 8:
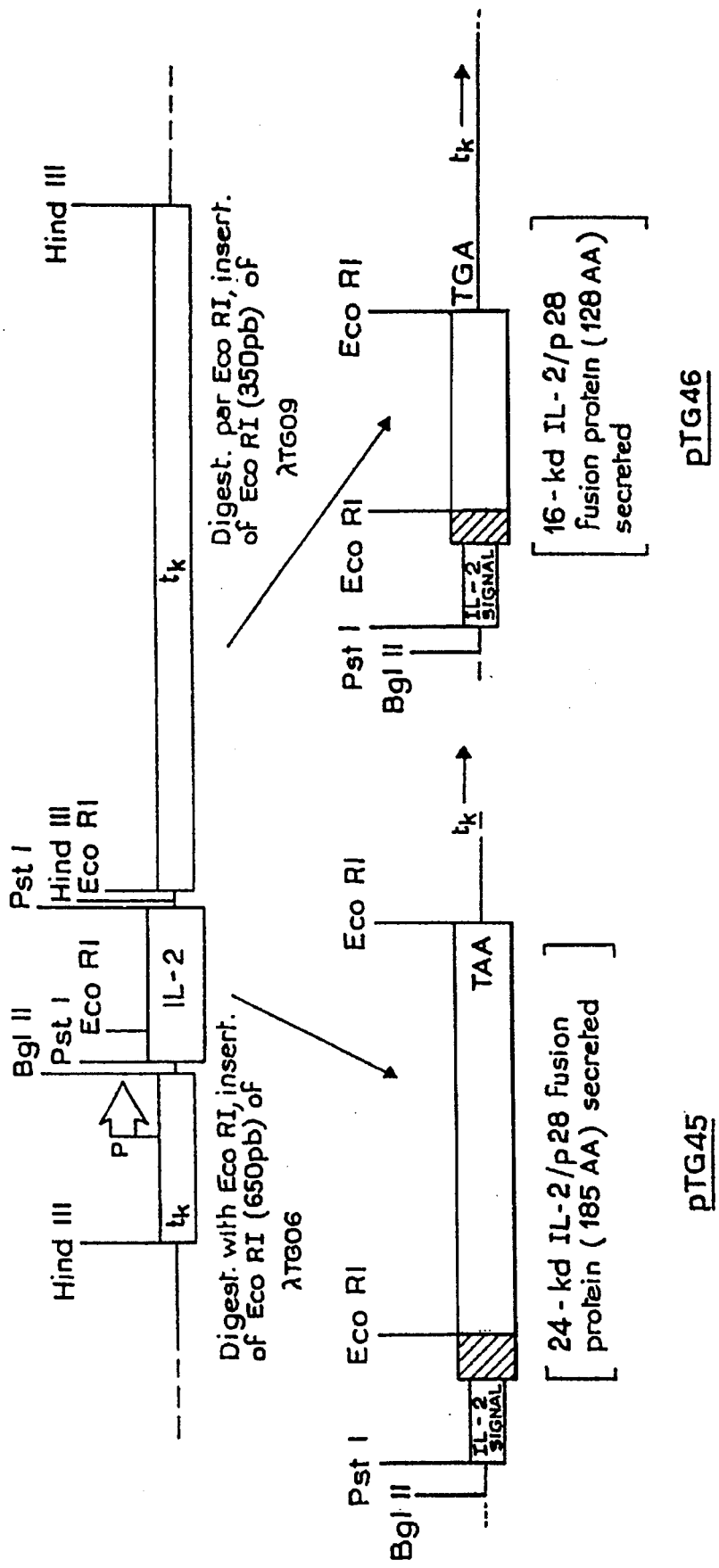

FIG. 8 shows the construction of pTG45 and pTG46 by insertion of the EcoRI fragments of λ TG06 and λ TG09 in the EcoRI site of pTG188-I (see construction of FIG. 7).

FIGS. 9a–9b show the structure of the IL2/p28 fusion protein encoded by pTG45. The presence is noted of a signal peptide which permits the excretion of a 24-kd protein that includes most of p28.

FIGS. 10a and 10b show the structure of the IL2/p28 fusion protein encoded by pTG46. The signal peptide permits the excretion of a 16-kd protein which contains the central portion of the p28 antigen.

Figure 11:
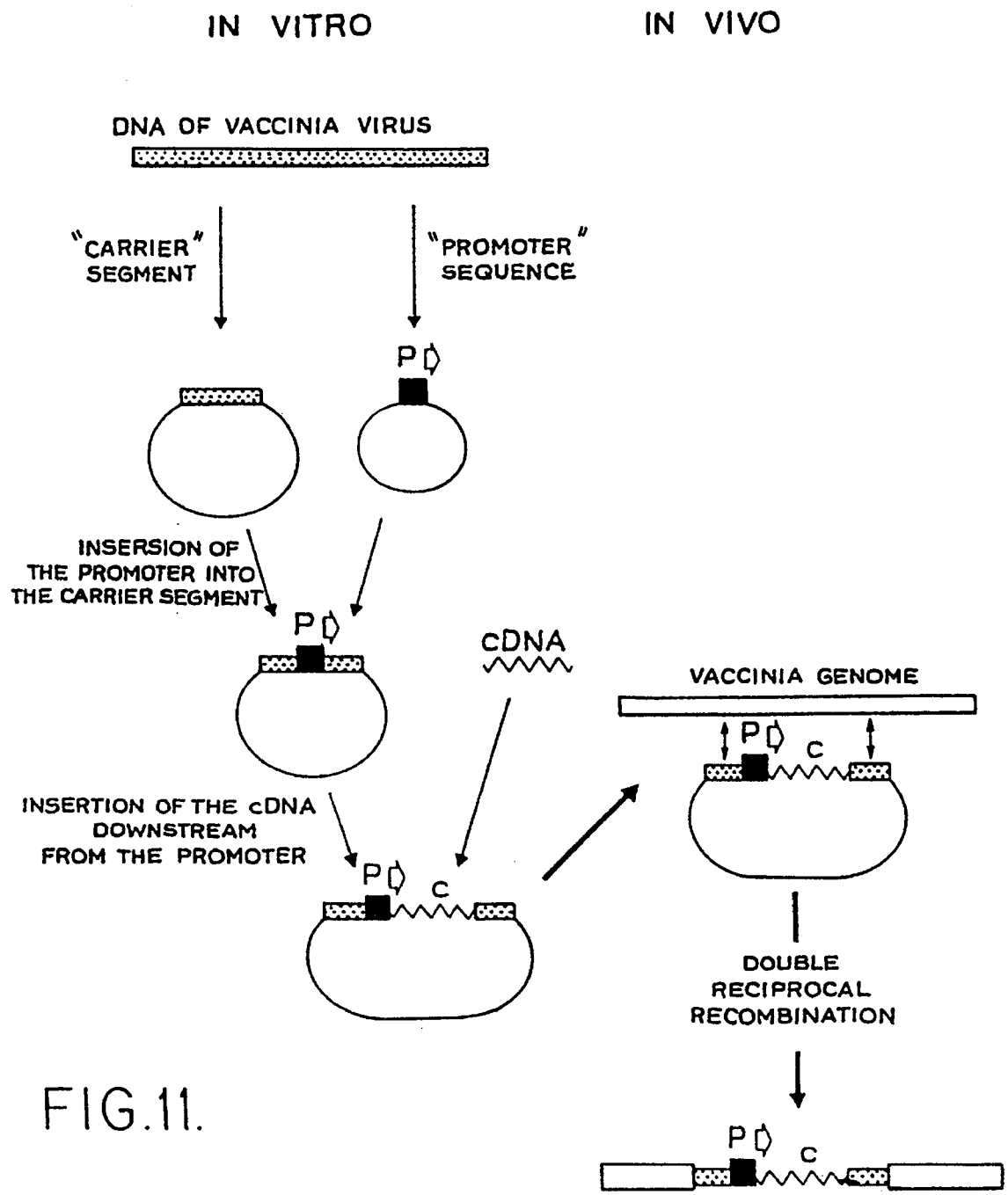

FIG. 11 shows the insertion of the gene coding for IL2/p28, placed under the control of the vaccinia 7.5K promoter, into a plasmid carrying the vaccinia TK gene. Insertion of this expression block into the viral genome by double recombination between the TK sequences.

Figure 12:
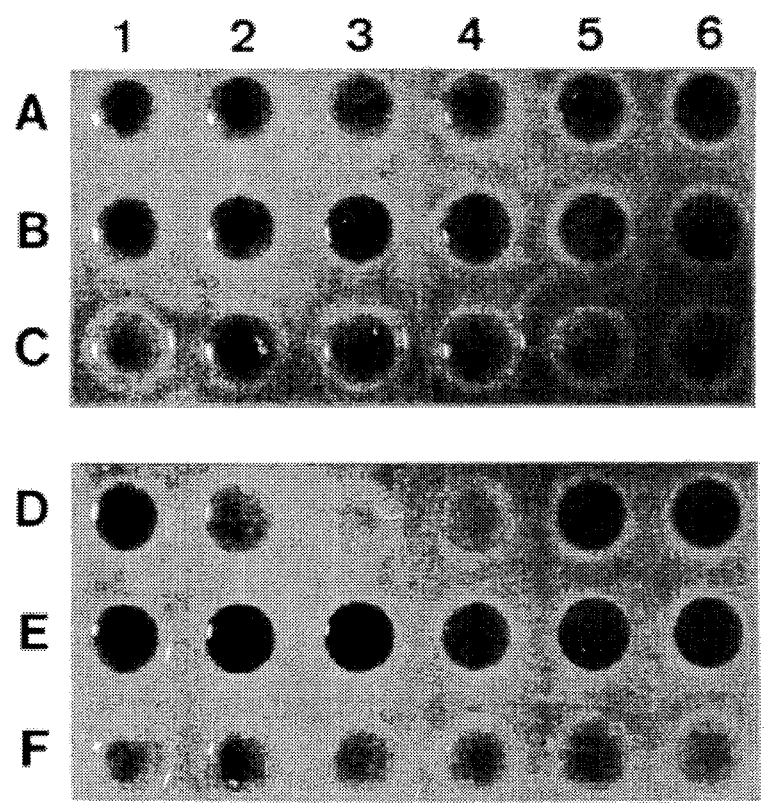

FIG. 12 shows the detection of the proteins secreted into the culture medium of BHK21 cells infected with the recombinant viruses VV.TG.p28 Sm-1 and VV.TG.p28 Sm-2, by means of the rabbit or rat antibody specific for the native p28.

A and D supernatant of VV.TG.p28Sm-1
B and E supernatant of VV.TG.p28Sm-2
C and F supernatant of culture infected with a wildtype VV
A, B, C detection with rabbit antibodies
D, E, F detection with rat antibodies.
The numbers correspond to independent isolations.

Figure 13:
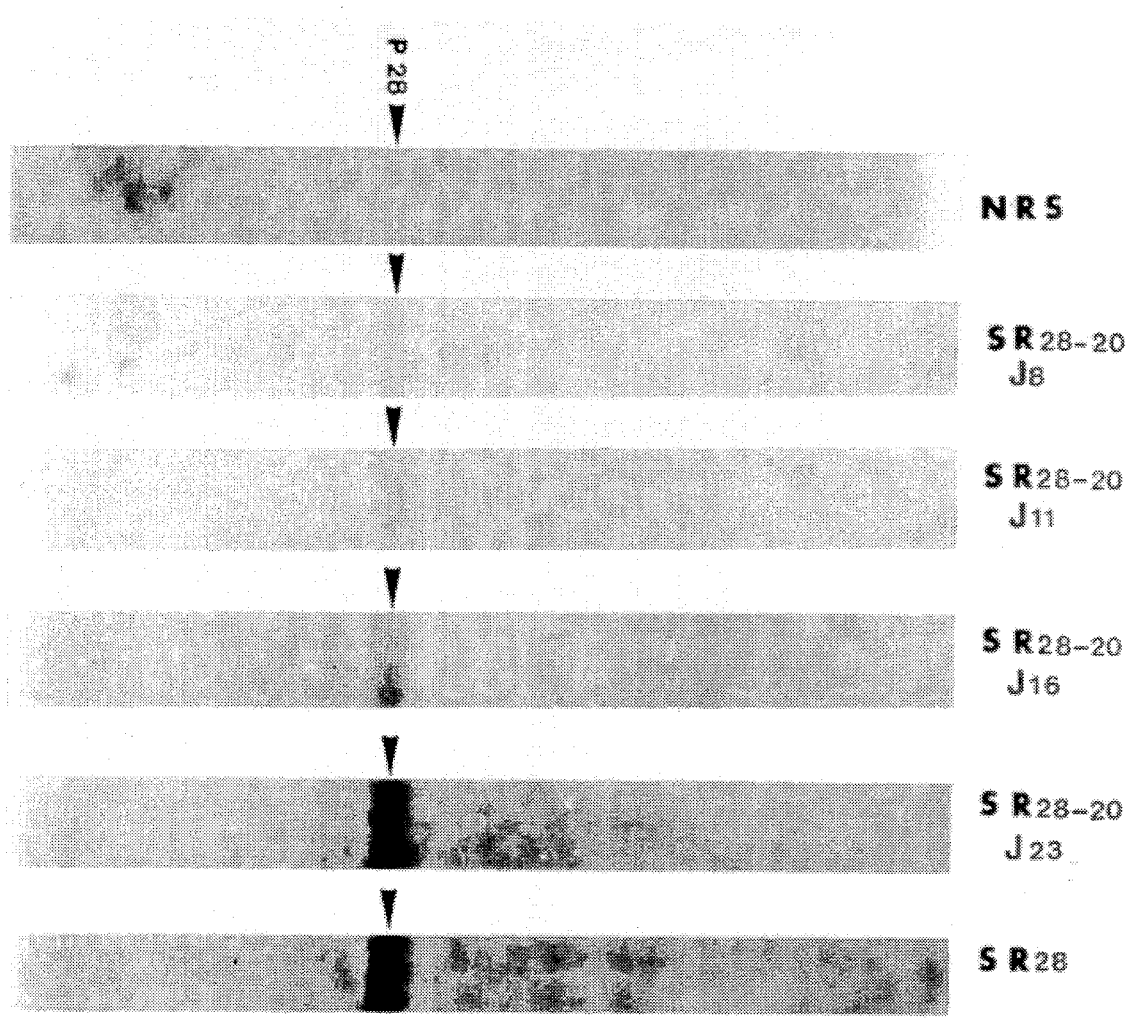

FIG. 13 shows the detection of the anti-p28 antibodies by the "Western blot" test with the native p28 protein, in the sera of rats immunized with the cII/p28 protein synthesized by E. coli.

NRS: serum of control, non-inoculated rat

SR28-20,D8, D11, D16, D23: serum of rats harvested 8, 11, 16 and 23 days after inoculation with the cII/p28 protein SR28: serum of rat inoculated with the native p28 protein.

Figure 14:
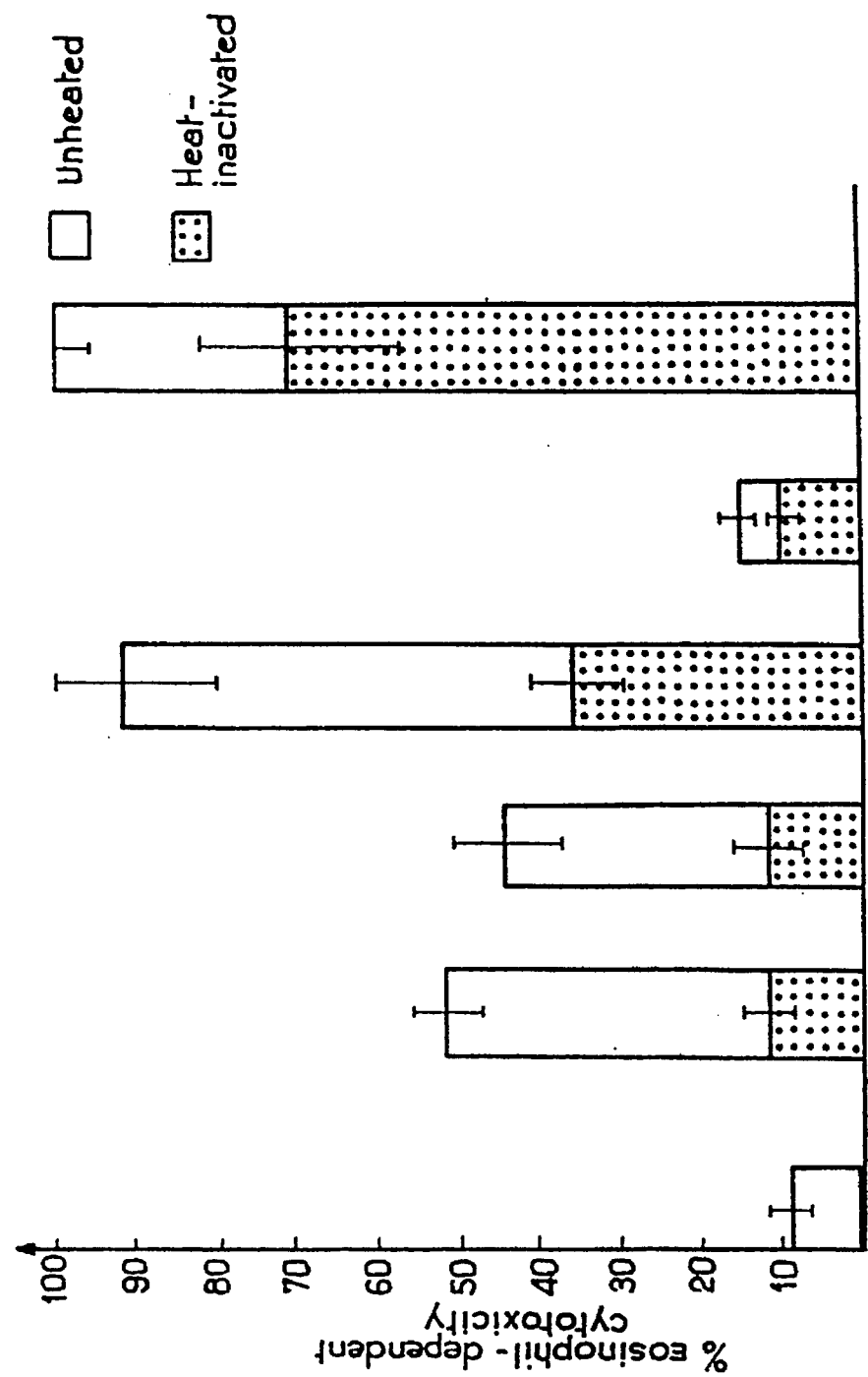

FIG. 14 shows the biological activity of the same sera as in FIG. 13, measured in a test of eosinophil-dependent cytotoxicity against schistosomula (see Tables I, II and III).

SR28-20 shows the antiserum directed against a 20-kd cloned fragment corresponding to the 28-kd antigen of S. mansoni recovered at different times after the second injection SR-28 shows the antiserum directed against native p28 and recovered 14 days after the second injection.

Figure 15:
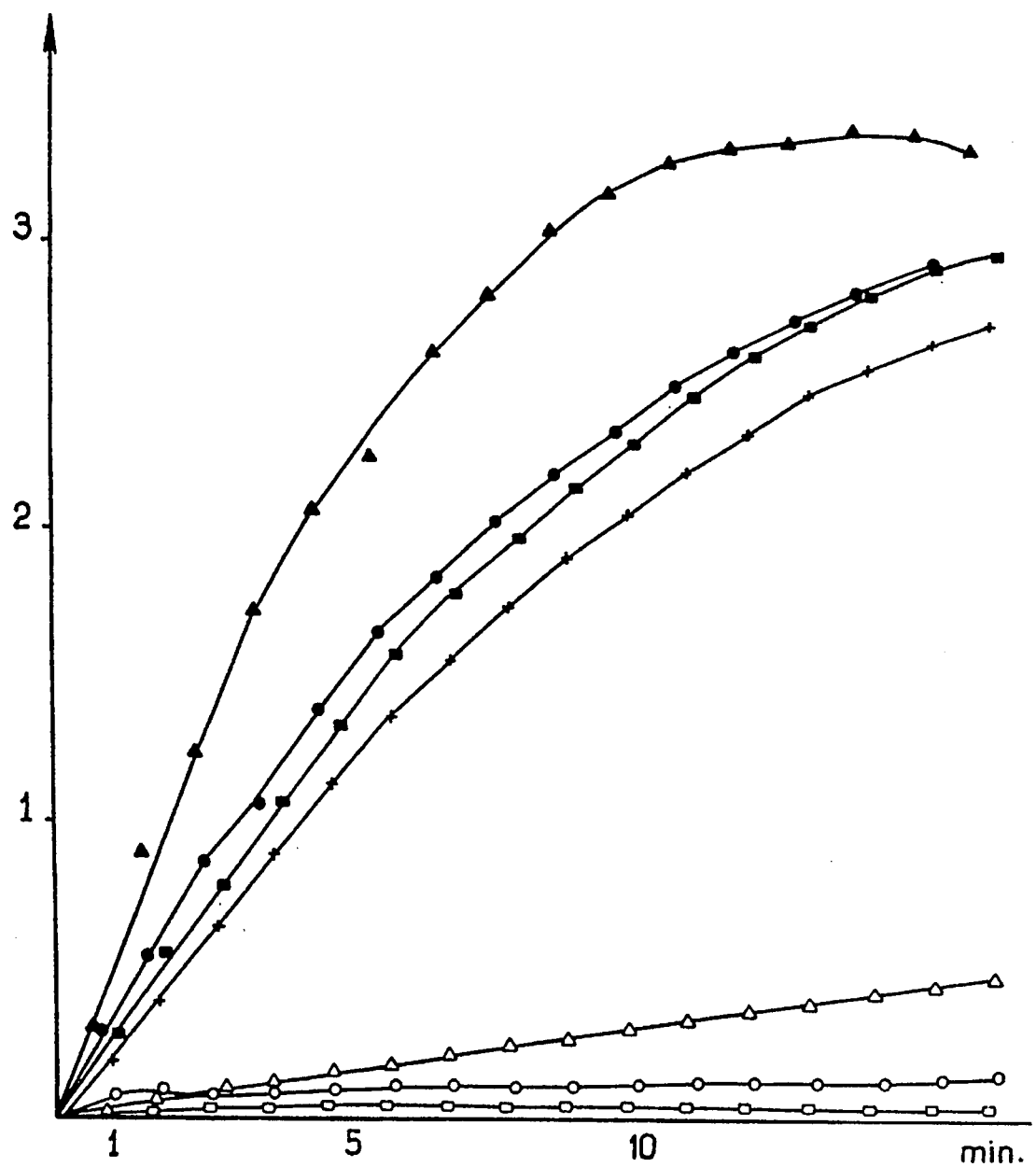

FIG. 15 shows the following curves:

GT of rat liver (▲9 μg . 6 μg)

crude extracts of E. coli, control (o) and TGE901/pTG54(■)

crude extracts of S. cerevisiae, control (o), transformed with a plasmid vector (Δ) and TGY2sp13b/pTG2800 (+).

FIGS. 16a–16c show the cDNA sequence of the p28II protein, as well as the corresponding protein sequence according to the 3 reading-frames.

Figure 17:
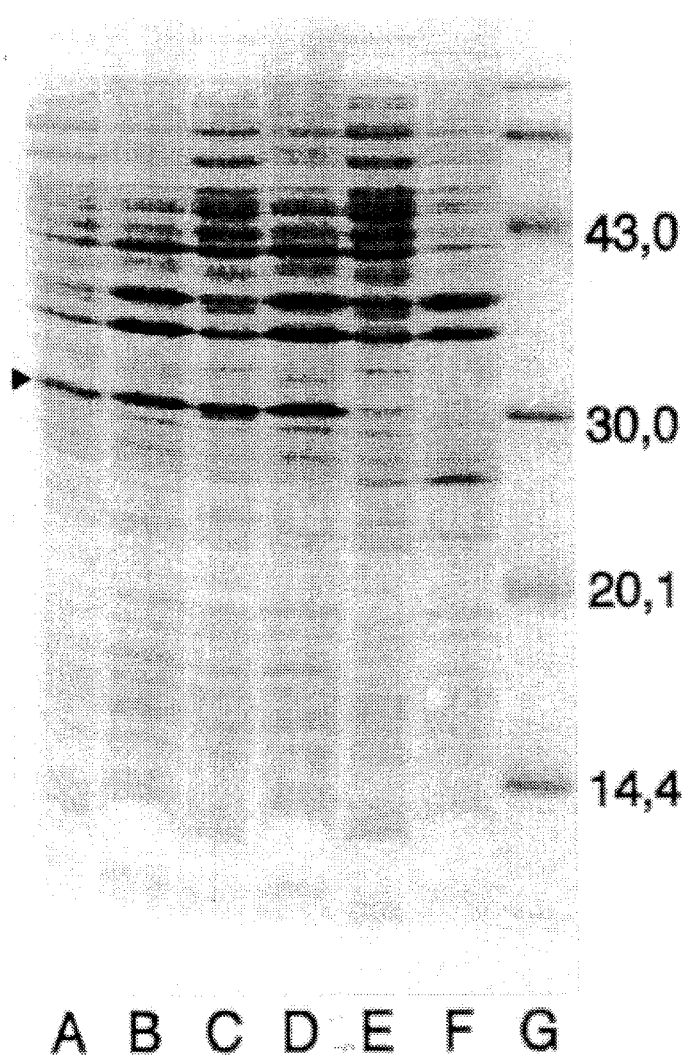

FIG. 17 shows an electrophoresis on acrylamide gel of E. coli extracts after staining with Coomassie blue:

A, C, and F total extract
B, D and E insoluble fraction of the same extracts
A, B, C, D E. coli TGE901/pTG56
E, F E. coli TGE901/pTG908 (control vector)
G molecular mass markers.

EXAMPLE 1

IDENTIFICATION AND CLONING OF A cDNA CODING FOR A p28 PROTEIN

The strategy chosen for cloning the gene coding for a p28 antigen whose sequence is unknown was to identify the expression products in *E. coli* of a schistosome cDNA library, using polyclonal antibodies specifically raised against the p28. These antibodies were induced by immunizing rabbits and rats with extracts, fractionated on gel, of the adult *S. mansoni* parasite.

Preparation of the cDNA library

From the RNA extracted from adult *schistosomes*, the complementary DNA strand is synthesized by the action of MLV reverse transcriptase. The DNA, made double-stranded by the action of the Klenow fragment of *coli* polymerase, is then treated with S1 nuclease to make its ends blunt. The fragments corresponding to the size sought, that is to say between 500 and 4,000 bp, are selected on a sucrose gradient. A tail of dG residues is added to these fragments and they a reinserted into the EcoRI site of the phage lambda derivative gt 10 (Huynh, 1984) via a synthetic adapter 5'-AATTC CCCCCCCCCC-3' (Le Bouc et al. 1986).

After ligation, the recombinant phages are packaged in vitro. A library of $2\times10^6$ phages thereby formed is then amplified by inoculation into *E. coli* POP 101 (Lathe, 1977).

After amplification, the phages are concentrated with PEG and purified by two CsCl gradient centrifugations, and their DNA is extracted. The cDNA inserts are recovered by digestion with EcoRI and purified on a sucrose gradient. The 500- to 2,000-bp fractions are then inserted into an expression vector, the phage lambda derivative gt 11 which permits the expression of foreign genes under the control of the lac promoter, after fusion of the cDNA with the β-galactosidase gene of *E. coli* (Young and Davis, 1983).

Screening of the library and selection of candidates

A sample of this library in lambda gt 11 is inoculated into *E. coli* strain Y1090 (Young and Davis, 1983) at a dilution representing $1\times10^5$ phages per dish 90 mm in diameter.

The induction of the expression of the protein under the control of the lac promoter is triggered at 42° C. in the presence of isopropyl-β-D-thiogalactopyranoside.

The synthesized proteins are adsorbed onto nitrocellulose filters and incubated in the presence of rabbit antibody specific for p28. The bound antibodies are recognized by a second, biotin-labeled anti-rabbit antibody; this complex is then visualized by means of a streptavidin-peroxidase reaction followed by staining with HRP (Bio-Rad).

This detection with antibody enables the recombinant phages to be identified in which the cDNA insert directs the synthesis of a protein or protein fraction carrying the epitopes recognized by the specific anti-p28 antibodies.

A first selection leads to 3 independent isolates, lambda TG06, lambda TG08 and lambda TG09, which contain cDNA inserts of 650, 700 and 350 base pairs, respectively.

The nucleotide sequences of the inserts carried by these candidates overlap and include a region which might correspond to the C-terminal region of a hypothetical protein having a molecular weight of 28 kd. A $^{32}$P-labeled synthetic nucleotide 5'-GGAATAGTTGGTTTGATT-3' complementary to the 5' end of the coding region of the insert of lambda TG06 was synthesized and used to perform a fresh screening of the cDNA library in lambda gt 10.

In this manner, two new candidates were able to be isolated, lambda TG10 and lambda TG11, both of which contain a complete nucleotide sequence coding for a protein of 211 amino acids and corresponding to a MW of 28 kd. Determination of the cDNA sequence carried by the recombinant phages and that of the corresponding protein The complete cDNA sequence (confirmed by determining the sequence for different candidates) and the primary amino acid structure resulting therefrom are shown in FIGS. 1a–1c.

This result and the work which is at present published provide no information about the N-terminal sequence of the initial product of translation of the native gene, nor about the possible existence of a precursor and a signal peptide preceding the mature protein.

Nevertheless, the exact localization of the first amino acid is not essential in the context of the invention, since the strategy adopted for the isolation of this gene and for its expression comprises the search for major epitopes which are present in the p28 and which are recognized by the host's immune system.

This reasoning will be used in the examples that follow, which describe the expression of the major epitopes in different organisms.

Expression of the p28 antigen

The general strategy developed for the expression of the antigenic epitopes present in the p28 was to fuse the cloned cDNA fragment in the correct reading-frame to a nucleotide sequence coding for the N-terminal region of an efficiently expressed and well characterized protein. The hybrid protein thereby obtained will generally be recognized by the antibodies raised against the native mature p28, and can be expected to induce an immune response against the parasite. With this working hypothesis, different host systems were used for analyzing the immunogenic properties of the fusion proteins, both in vivo and in vitro, and they will be developed in the examples which follow.

EXAMPLE 2

EXPRESSION IN *E. COLI*

To obtain the expression of a p28 antigen in *E. coli*, a derivative of the expression plasmid pTG908, described in patent application 83/00,909, was used for synthesizing a fusion protein whose structure is shown in FIGS. 3a and 3b.

The vector pTG908 contains an origin of replication, the $P_L$ promoter of bacteriophage lambda and the cII ribosome binding sequence including the N-terminal end of the cII gene with suitable restriction sites downstream from the translation initiation signal. The BamHI site 39 bp downstream from the ATG codon was used for inserting an EcoRI site by means of a double-stranded adapter comprising the following oligomers:

The resulting plasmid, pTG1924, contains a single EcoRI site with the GAA codon in phase with the initiation codon of the cII gene. All the cDNA inserts originating from the lambda gt11 recombinants which gave a positive signal after selection with the anti-p28 serum were inserted directly into this site. When the insert is present in the correct orientation, this gives a nucleotide sequence coding for the N-terminal end of the cII gene and continuing in phase with the cDNA sequence coding for the p28 antigen, or for a portion of the latter.

Figure 2:
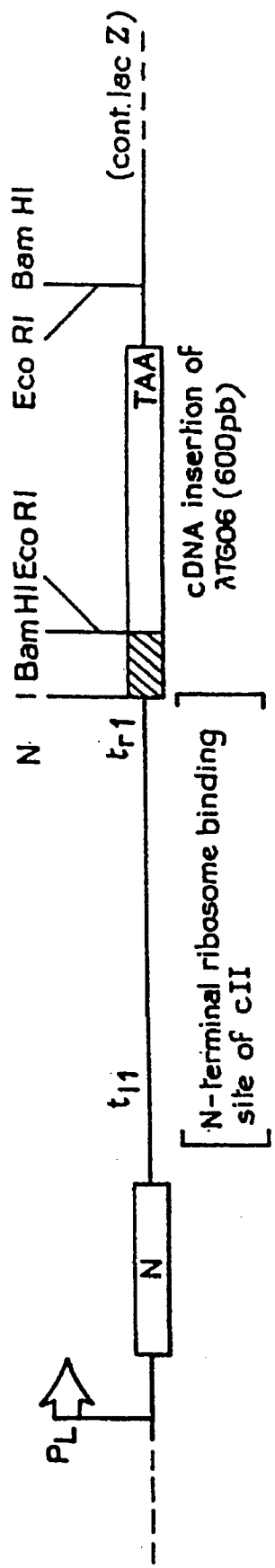
FIG. 2 shows the construction of pTG44 by integration of an EcoRI insert of λ TG06 in pTG1924. pTG1924 is a derivative of pTG908 with an EcoRI site placed in phase, situated 46 bp downstream from the initiation codon of cII. pTG44 codes for a cII/p28 fused protein having a molecular weight of 25 kd.

One of the resulting plasmid constructions, pTG44, containing the insertion into this EcoRI site of the fragment derived from lambda TG06, is shown in FIG. 2. The sequence of the cII/p28 fusion protein, with a calculated molecular weight of 25 kd, is given in FIGS. 3a and 3b.

A culture of *E. coli* N4830 transformed with pTG44 is grown on LB medium to an $OD_{600}$ of 0.2, and the synthesis thesis of the fusion protein is then induced by raising the temperature to 42° C. for the following 8 hours.

Figure 4:
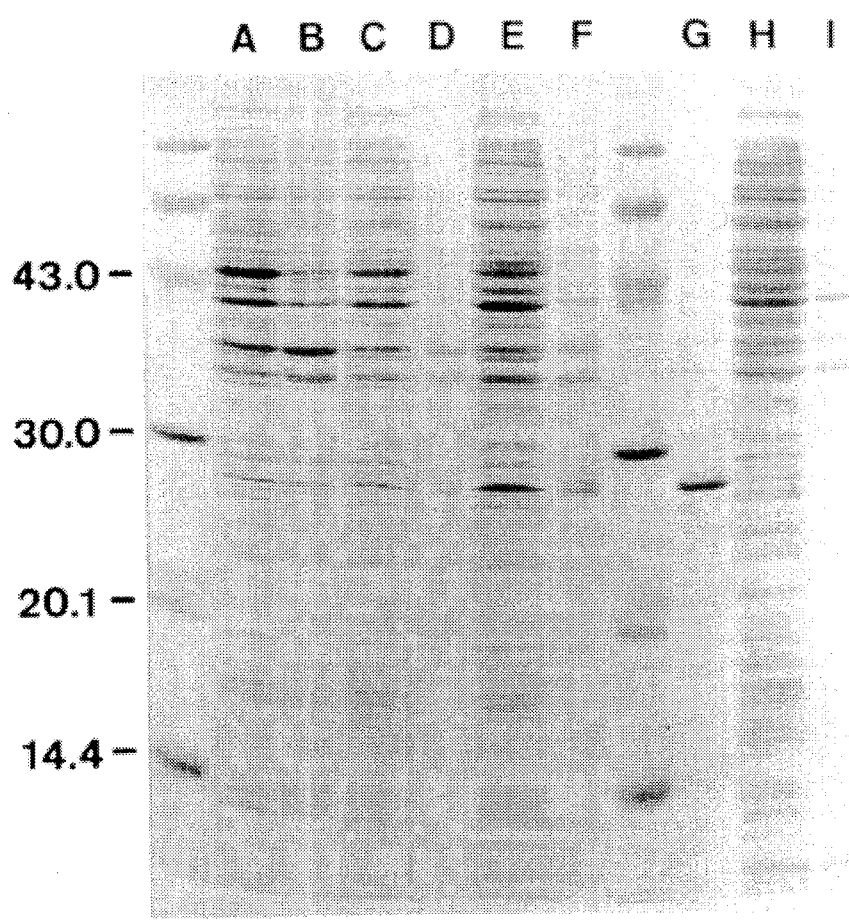
FIG. 4 shows total extracts and insoluble fractions of the extracts of E. coli TGE901 pTG44 after electrophoresis on SDS-acrylamide gel and staining with Coomassie blue.

On completion of the culturing, the cell extracts were analyzed on SDS-acrylamide gel by staining with Coomassie blue (FIG. 4). The cII/p28 fusion product is recovered in the insoluble fraction obtained after lysis of the cells by sonication. The protein is recovered with a purity of the order of 80% by extracting the insoluble fraction in the presence of 0.2% SDS. Analysis of the final preparation by "Western blotting" shows that this particular protein is efficiently recognized by the rabbit antibodies raised against the native p28 antigen (FIG. 5).

EXAMPLE 3

EXPRESSION IN YEAST S. CEREVISIAE

Two types of constructions were carried out to express the p28 cDNA in yeast: the first leads to a fusion protein comprising, on the N-terminal side, the first 22 amino acids of yeast phosphoglycerate kinase (PGK); the second gives a protein resembling the natural mature protein.

CONSTRUCTION OF A VECTOR CARRYING A FUSION OF GENES CODING FOR PGK AND p28 (pTG1886)

1) The EcoRI insert of lambda TG10 containing the cDNA of the p28 protein was introduced into a coli/yeast shuttle plasmid, pTG836.

This plasmid is a derivative of pBR322 which contains the origin of replication of the 2-micron plasmid of yeast, th e URA 3 gene (patent 84/12,598) and the yeast PGK gene (Hitzemann et al. 1982).

A single EcoRI site was introduced between the BamHI site (situated 20 codons downstream from the PGK initiation codon) and the SalI site (present in the pBR322 sequence) by inserting a synthetic adapter:

```
5'-GATCTGAATTCAGATCTC-3'
3'-ACTTAAGTCTAGAGAGCT-5'
``` the resulting plasmid being pTG1880.

The insertion of the EcoRI fragment of lambda TG10 in the EcoRI site of pTG1880, in the correct orientation, gives pTG1883.

2) The PGK/p28 expression block carried by this plasmid will be recovered and inserted in an expression vector for yeast, pTG848 (French patent 85/06,672). This requires an intermediate manipulation in phage M13:

A HindIII-BglII fragment containing the PGK/p28 expression block is inserted in M13TG131 (Kieny et al. 1983) between the HindIII and BamHI sites, to give M13TG1884.

As a result of the existence of neighboring restriction sites, this construction enables the same expression block to be recovered in the form of an SmaI-BglII fragment.

This fragment is then introduced between the SmaI and BglII sites of the expression vector pTG848.

The resulting plasmid is pTG1886.

3) Yeast TGY1sp4 was transformed with this plasmid pTG1886.

Crude cell extracts of these cultures were analyzed by electrophoresis on SDS—acrylamide gel and by the "Western blot" technique. FIGS. 5 and 6 show clearly the appearance of a new protein band having an MW of 30 kd, as expect ed for the PGK/p28 fusion protein, and which is recognized by the antibodies raised against the native p28 extracted from the schistosomes.

CONSTRUCTION OF AN EXPRESSION VECTOR CARRYING ONLY THE p28 cDNA, UNDER THE CONTROL OF THE PGK PROMOTER

1) In the M13TG1884 construction described above, the initiation codon for the p28 protein is preceded by the first 22 codons of the PGK gene and by 8 codons due to the cloning technique (especially dC residues). These 90 additional base pairs were deleted by in vitro mutagenesis of the single-stranded M13TG1884 in the presence of the oligonucleotide:

5'-CAACAAAATATAAACA [ATG] GCTGGCGAGCATATC-3' which corresponds to the first 16 nucleotides of the PGK mRNA leader sequence followed by the nucleotides of the beginning of the p28 coding sequence; between these two sequences, there is the ATG which coincides with both the initiation ATG of the PGK and that of p28.

2) The correctly deleted derivative M13TG1884m was digested with SmaI and BlgII and the fragment carrying the non-fused p28 cDNA, placed under the control of the PGK promoter, was inserted in the expression vector pTG848 (as described above) to give pTG1885.

3) The yeast TGY1sp4 was transformed with this plasmid pTG1885.

Crude cell extracts of these cultures were analyzed by electrophoresis on SDS-acrylamide gel and by the "Western blot" technique. FIGS. 5 and 6 show clearly the appearance of a new protein band having an MW of 28 kd, and which is recognized by the antibodies raised against the native p28 extracted from the schistosomes.

EXAMPLE 4

EXPRESSION IN RECOMBINANT VACCINIA VIRUSES a) Construction of a recombinant vaccinia virus which expresses a p28 fused to the first amino acids of IL-2.

The cDNAs carried by the phages lambda TG06 and TG09 were introduced into suitable vectors so that they could subsequently be inserted into the genome of vaccinia virus, and thereby be expressed in mammalian cells.

The vectors according to the present invention are derived from the vectors which were employed for the expression of human interleukin-2 (see French Patent No. 85/09,480). A derivative of pTG188 was thus constructed which contains an EcoRI site in a region of the nucleotide sequence which corresponds to 9 amino acids downstream from the N-terminal alanine residue of native interleukin-2 (FIG. 7). The lambda TG06 and lambda TG09 cDNA inserts were inserted in the correct orientation between the EcoRI sites of pTG188-I, to give plasmids pTG45 and pTG46 which code for an IL-2/p28 fusion protein having a molecular weight of 24 kd and 16 kd, respectively, (FIG. 8), as shown in FIGS. 9a and 9b, FIGS. 10a and 10b. The Presence of a signal peptide upstream from the construction permits the secretion of the protein into the culture medium.

The major portions of plasmids pTG45 and pTG46 contain the TK viral gene interrupted by the sequence coding for the IL-2/p28 fusion protein, this sequence being placed under the control of an efficient promoter, that for the 7.5K vaccinia protein.

These sequences inserted into the TK gene of vaccinia can be transferred into the genome of vaccinia virus by a double reciprocal recombination (FIG. 11), as described previously (Panicalii and Paoletti, 1982; Mackett et al., 1982; Kieny et al., 1984).

The recombinant viruses VV.TG.p28Sm-1 and VV.TG.p28Sm-2 containing the cDNAs derived from lambda TG06 and lambda TG09, respectively, are used for infecting a monolayer of BHK21 cells. After 24 hours at 37° C., the culture supernatant is tested to determine the presence of the IL-2/p28 fusion protein, this being performed by adsorption onto a nitrocellulose filter and incubation with rat or rabbit antibodies specific for the native p28.

The detection of the bound antibodies is performed by incubation with a biotin-coupled antiserum raised against rat or rabbit whole immunoglobulins; this complex is then visualized by means of a streptavidin-peroxidase reaction and final staining in the presence of an HRP staining reagent (Bio-Rad).

For both V V.TG.p28Sm-1 and VV.TG.p28Sm-2, specific antigens (more than 100 ng/ml) can be detected (FIG. 12) in the culture medium, this being the case for different independent recombinants, whereas the supernatants of cells infected only with the wild-type virus do not give a significant signal.

b) Construction of a recombinant vaccinia virus which expresses a p28 fused to the signal peptide of the rabies glycoprote in (VV.TG.1184).

Construction of the bacteriophage M13TG177

The bacteriophage M13TG169 (French patent 86/05,043) contains the coding sequence of the env gene of the HIV-I virus, flanked at the 5' end by the sequence coding for the signal peptide of the rabies glycoprotein and at the 3' end by the sequence coding for the transmembrane region and the intracytoplasmid region of the rabies glycoprotein.

An EcoRI site was introduced between the KpnI and HindIII sites of M13TG169 to generate M13TG176, having the following structure:

S: signal of the rabies gp
TM: transmembrane region of the rabies gp
The EcoRI site situated downstream from the peptide signal was then eliminated by localized mutagenesis using the following oligonucleotide:
+tm 5' GGGGAAATCGTAATC 3'

The resulting bacteriophage M13TG177 hence possesses a single EcoRI site.

Construction of the bacteriophage M13TG1105

The EcoRI restriction fragment of λ TG10 containing the coding sequence for the p28 is introduced into M13TG177 to generate M13TG1105, having the following structure:

Construction of the bacteriophage M13TG1108

The first two amino acids following the peptide signal S are fused in phase with the coding sequence for the p28 by localized mutagenesis with the following oligonucleotid
+tm       5'CTTGATATGCTCGCCAGCAATAGG-GAATTTCCCAAA 3'

The resulting bacteriophage is referred as M13TG1108.

Construction of plasmid pTG1184

The bacteriophage M13TG1108 is partially digested with PstI in order to isolate the fragment containing the whole of the sequence coding for the p28, and inserted at the PstI site of plasmid pTG186POLY to generate pTG1184.

c) Construction of a recombinant vaccinia virus which expresses a p28 fused to the signal peptide and to the transmembrane region of the rabies glycoprotein (VV.TG.1185)

Construction of the bacteriophage M13TG1109

In the bacteriophage M13TG1108, the Last amino acid before the translation termination codon is fused in phase with the first amino acid of the transmembrane region TM by virtue of the following oligonucleotide:

5'TGCACTCAGTAATACATAGAAGGGAGTTGCAGGCCT3'

The resulting bacteriophage is referred to as M13TG1109.

Construction of plasmid pTG1185

As for the construction of pTG1184, the bacteriophage M13TG1109 is subjected to partial digestion with PstI and the fragment containing the whole of the sequence coding for the p28 is inserted at the PstI site of pTG186POLY to generate pTG1185.

d) Characterization of the viruses VV.TG.1184 and 1185

Plasmids pTG1184 and 1185 are used for transferring the gene coding for the p28 into the genome of vaccinia virus as described above.

The virus VV.TG.1184 expresses the p28 fused to the signal peptide of the rabies glycoprotein.

The virus VV.TG.1185 expresses the p28 fused to the signal peptide and to the transmembrane region of the rabies glycoprotein.

BHK21 cells are infected with VV.TG.1184 or 1185 viruses (0.2 puf/cell) for 16 hours. After addition of [$^{35}$S] methionine for 4 h, the labeled proteins are immunoprecipitated using a rabbit antibody directed against the p28. In the case of the virus VV.TG.1184, a band corresponding to a molecular weight of 28 kd is demonstrated. This protein is also present in abundance in the culture supernatant, showing that the protein is secreted.

In the case of the virus VV.TG.1185, a band corresponding to a molecular weight of 35 kd is demonstrated. This protein is absent from the culture supernatants, demonstrating that it is retained in the cell membrane by the transmembrane region of the rabies glycoprotein.

EXAMPLE 5

VACCINATION OF ANIMALS WITH THE p28 ANTIGEN PRODUCED BY GENETIC MANIPULATION

The biological effect of the recombinant proteins containing one or more major-epitopes of native p28 was analyzed in comparison with the response observed after immunization of rats with the mature native p28 isolated from total extracts of adult parasites. The fusion proteins produced both by microorganisms such as *E. coli* or *S. cerevisiae* or by recombinant vaccinia virus may be a used for such an approach, but only the results obtained with the cII/p28 fusion protein are detailed below.

IMMUNIZATION OF RATS 20 3-month-old "Fischer" male rats are immunized by intraperitoneal injection with 50 µg of a cII/p28 fusion protein (Example 2) in the presence of Freund's adjuvant, The animals receive a second dose after 2 weeks and the antisera are drawn starting on day 8.

4 pools of sera each comprising 5 samples are assayed in triplicate to test for the presence of antibodies which recognize the native p28 protein and the cytotoxicity of the sera with respect to schistosomula.

DETECTION OF SPECIFIC ANTIBODIES

The sera of rats immunized with the cII/p28 protein extracted from *E. coli* are assayed in a "Western blot" test for their reaction against the p28 of a whole extract of adult parasites, the p28 being separated by electrophoresis on SDS-polyacrylamide gel. FIG. 13 shows unambiguous recognition of the native p28 protein by these sera.

The maximal intensity of this response is attained on day 23 and is virtually equal to that observed with the sera of animals immunized with the native antigen.

ASSESSMENT OF THE EOSINOPHIL-DEPENDENT CYTOTOXICITY

The same sera were assessed in a test of eosinophil-dependent cytotoxicity according to the technique described by Capron et al. (1981):

50 schistosomula of *S. mansoni* are incubated in the presence of each test serum (unheated), or of appropriate controls, and in the presence of eosinophils (Lou rat non-adherent peritoneal cells containing from 40% to 70% of eosinophils). The reaction mixture comprises 6000 effector cells for 1 schistosomulum, in a total volume of 200 µl. After 48 hours' incubation at 37° C., the percentage mortality of the schistosomula is assessed by microscopic examination.

The results shown in Table I show clearly the presence of a cytotoxic factor capable of inducing a high level of mortality of the schistosomula, the level being very close to that induced by a serum of a rat infected with *S. mansoni*.

DEMONSTRATION OF THE ROLE OF SPECIFIC IgE's IN THE CYTOTOXICITY REACTION

The same cytotoxicity test was performed with heated serum (2 hours at 56° C.) and with heated serum to which complement was added. The results shown in Table II show that the factor responsible for the cytotoxicity is temperature-sensitive and that this loss in activity cannot be compensated by adding complement.

In addition, it is possible to remove the IgE's selectively from the test sera by adsorption with a goat antiserum specific for rat IgE's, coupled to Sepharose B. The sera treated in this manner and then dialyzed are tested for their eosinophil-dependent cytotoxic activity.

Table III shows that the selective depletion of the rat sera in respect of IgE prevents the expression of the cytotoxicity. The latter is hence very specific to the IgE's of the sera of rats immunized with the cII/p28 protein.

DEMONSTRATION OF THE PROTECTION OF ANIMALS AGAINST A TEST INJECTION WITH CERCARIAE

Fischer rats were injected (as described above) with the p28 antigen produced in *E. coli* or in yeast, in the presence of aluminum hydroxide, or with which expresses the p28 antigen, VV.TG.1185 ($5 \times 10^7$ pfu of recombinant virus per animal). The control animals are injected with aluminum hydroxide alone.

Six weeks after the immunization, the animals are infected subcutaneously with 1,000 cercariae (infectious larval state of the schistosome).

21 days after the test inoculation, the rats are sacrificed and their content of adult parasites is assessed. The latter are harvested by perfusion of the hepatic portal vein with physiological saline and then counted.

A reduction is observed in the parasite content compared with the controls, equivalent to:

64±4% with the antigen produced in *E. coli*

70±10% with the antigen produced in yeast

60±8% with the antigen produced by vaccinia.

TABLE I

Test of eosinophil-dependent cytotoxicity
Study of the sera of rats immunized with the cII/p28
protein produced in *E. coli*.

| Source of antibody | Final dilution of the serum | % cytotoxicity after 48 hours' incubation |
|---|---|---|
| Serum of rat immunized with cII/p28, harvested on day | | |
| D8 | 1/16 | 60.5 ± 2.5 |
|  | 1/32 | 55.5 ± 5 |
|  | 1/64 | 6.5 ± 6.5 |
| D10 | 1/16 | 85.5 ± 0.5 |
|  | 1/32 | 76 ± 3.5 |
|  | 1/64 | 57 ± 4.7 |
| D16 | 1/16 | 85.5 ± 0.5 |
|  | 1/32 | 78 ± 6 |
|  | 1/64 | 52 ± 3 |
| D23 | 1/16 | 88 ± 3.5 |
|  | 1/32 | 92 ± 0 |
|  | 1/64 | 52 ± 11.5 |
| Serum of rat infected with *S. mansoni* | 1/16 | 97 ± 1 |
| Serum of healthy rat | 1/16 | 0 |

TABLE II

Eosinophil-dependent cytotoxicity
Study of the participation of complement

| Serum of rat immunized with the cII/p28 protein produced by *E. coli* (final dilution: 1/16) 16 days after immunization | % cytotoxicity after 48 hours' incubation |
|---|---|
| Unheated serum | 85.5 ± 0.5 |
| Heated serum | 26.5 ± 5.5 |
| Heated serum + guineapig complement | 38.5 ± 0.5 |
| Heated serum + heated guineapig complement | 21.5 ± 1.5 |

TABLE III

Eosinophil-dependent cytotoxicity
Study of the participation of antibodies of IgE isotype

| Source of antibodies | % ctyotoxicity after 48 hours' incubation |
|---|---|
| Serum of rat immunized with cII/p28 produced in *E. coli*, harvested on day | |
| D16 | 48.5 |
| D23 | 40 |
| Serum of healthy rat | 0 |
| Anti-IgE column effluent | |
| D16 | 0 |
| D23 | 0 |
| Serum of healthy rat | 0 |

EXAMPLE 6

The glutathione S-transferase activity was demonstrated in the extracts of *E. coli* TGE901/pTG54 and *S. cerevisiae* TGY2s p13b/pTG2800 which express the p28I protein of *Schistosoma mansoni* (pTG2800 differs from pTG1894 described in Example 3 only in respect of a deletion of 170 bp in the ura3 gene promoter region).

The cultures are centrifuged and the pellets resuspended in buffer (100 mM Tris-HCl pH 7.5, 1 mM DTT). The yeast is ground with glass beads; the bacteria are treated with ultrasound. The extracts are centrifuged to remove the cell debris and the activity is measured in the supernatant (according to the techniques published by Moore et al. 1986 and Habig et al. 1974). From 40 to 100 μl of crude extract, 10 μl of 100 mM CDNB reagent (1-chloro-2,4-dinitrobenzene dissolved in 100% ethanol) and 1 ml of 100 mM $KH_2PO_4$ (P H 6.5)/2.5 mM reduced glutathione are mixed in a spectrophotometer cell.

As a positive control, rat glutathione S-transferase (provided by Sigma) was used at a final concentration of 9 μg and 6 μg per test.

As negative controls, an extract of *E. coli* TGE901/pTG959 carrying a vector without a p28 sequence and an extract of *S. cerevisiae* TGY2sp13b and TGY2sp13b/pTG848 carrying a vector without a p28 sequence were used.

All the extracts of bacteria and yeast are adjusted to a total protein concentration of 0.33 mg/ml.

A yellow color appears in the cells where there is glutathione transferase activity. The change in OD is measured in the spectrophotometer at 340 nm every minute for 15 minutes.

The results shown in FIG. 15 show that the extracts of *E. coli* and *S. cerevisiae* which contain the recombinant p28 protein show strong glutathione S-transferase activity.

EXAMPLE 7

SCREENING OF THE LIBRARY AND SELECTION OF THE λTG07 CANDIDATE

Screening of the cDNA library in λ gt11, described in Example 1, enabled several types of candidates to be visualized.

By immunodetection with a rat polyclonal antibody (induced by injecting the p28 purified from schistosomes), a new candidate, λ TG07, was selected which is not recognized by the synthetic probes which were used for selecting the candidates λ TG10 and λ TG11 described in Example 1, and whose sequence is hence different. Since the protein is recognized by the same anti-p28 antibodies, this new protein will be referred to as p28II, (and that which had been identified previously will be referred to as p28I).

EXAMPLE 8

DETERMINATION OF THE cDNA SEQUENCE CARRIED BY THE PHAGE λTG07

Various restriction fragments of the cDNA were recloned in M13 and sequenced.

The complete cDNA sequence and the primary amino acid structure which can be deduced therefrom (in the 3 reading-frames) are shown in FIGS. 16a–16c.

EXAMPLE 9

CREATION OF A BamHI SITE AT THE BEGINNING OF THE cDNA SEQUENCE

To facilitate the insertion of the cDNA into a suitable expression vector, a BamHI site was created at the beginning of the coding sequence by directed mutagenesis.

The mutagenesis was performed on the DNA cloned into M13 with the following synthetic oligomer, which is a 21-mer complementary to nucleotides 18 to 38 of the sequence shown in FIG. 1a, with the exception of the nucleotides to be mutated:

5' GTAAGGAGCGGATCCACGATG 3'
<u>BamHI site</u>

The cDNA sequence can hence be recovered in the form of a BamHI fragment, a second BamHi site being present in the M13 polylinker, downstream from the coding sequence.

EXAMPLE 10

EXPRESSION OF THE p28II PROTEIN IN *E. COLI*

The cDNA sequence coding for p28II was recovered in the form of a BamHI fragment and introduced into the expression vector pTG908, in the BamHI site.

The structure of the recombinant obtained is identical to that shown schematically in FIG. 2.

This vector contains an origin of replication, the $P_L$ promoter of phage lambda and the cII ribosome binding sequence including the N-terminal end of the cII gene, with a BamHI restriction site 39 bp downstream from the translation initiation site.

The p28II cDNA insert is hence present in phase with the N-terminal end of the cII gene.

A recombinant plasmid carrying the insert in the correct orientation was selected, pTG56, and the construction was checked by sequencing.

An *E. coli* TGE901 culture transformed by this plasmid is cultured on LB medium to an $OD_{600}$ of 0.2; the synthesis of the cII/p28II protein is then induced by increasing the temperature to 42° C. for the following 8 hours.

On completion of culturing, the cell extracts are recovered after treatment with ultrasound, and analyzed after electrophoresis on SDS-acrylamide gel and staining with Coomassie blue (FIG. 17).

A band of apparent molecular mass 28K is distinctly visible in the TGE901/pTG56 extracts (FIG. 17: bands A, B, C, D).

Analysis by "Western blotting" of a purified preparation of this protein extracted from *E. coli* shows that it is recognized by the rat antibodies directed against the native p28 purified from the schistosomes.

Possible glutathione S-transferase enzyme activity was tested for, but the test is negative. This negative result was expected, given the absence of homology between the sequences of the 2 p28 proteins.

EXAMPLE 11

VACCINATION OF RATS WITH THE p28II ANTIGEN PRODUCED BY *E. COLI*

The rats are immunized according to the protocol described in Example 5, and their sera are assessed in an eosinophil-dependent cytotoxicity test.

The results shown in Table IV show that the cytotoxic capacity of these sera is comparable to that of rats immunized with the first antigen p28I or with the native p28.

TABLE IV

Test of eosinophil-dependent cytotoxicity: study of the sera of rats immunized with the native p28 protein, and cII/p28 and cII/p28II produced in *E. coli* (dilution of the serum 1/16).

| Rats immunized with: | % cytotoxicity of the serum harvested on day | | |
|---|---|---|---|
| | 7 | 14 | 21 |
| Native p28 | 52.5% | 29% | 73% |
| cII/p28I-coli | 24.5% | 20% | 59.5% |
| cII/p28II-coli | 55% | 68% | 61.5% |
| Adjuvant alone (BSA + Pertusis) | | 30% | |
| Uninjected rats | | 0% | |
| Rats infected with *S. mansoni* | | 89.5% | |

The antibodies of rats immunized with the p28II protein produced in *E. coli* do not recognize the p28I protein. Similarly, the antibodies of rats immunized with the p28I protein produced in *E. coli* do not recognize the p28II protein. However, both types of antibodies recognize the native p28 preparation purified from the schistosomes, and the antibodies raised against the native p28 recognize both recombinant proteins.

This result is explained by a heterogeneity of the preparation of native p28 purified from schistosomes. Careful observation of the immunoprecipitation after 2-dimensional migration on gel of the native p28 protein or that translated in vitro on the mRNAs of schistosomes reveals the existence of a minor band which represents the splitting of the 28K band [Figure published by J. M. Balloul, R. J. Pierce, J. M. Grzych and A. Capron, Mol. Biochem. Parasit-ology 17 (1985) 105–114]. This minor band must correspond to p28II. Deposition of strains The following strains were deposited with the Collection Nationale de Culture de Microorganismes (National Collection of Microorganism Cultures), 28 rue du Docteur Roux—75724 Paris:

The *E. coli* strain N 4830, mentioned in Example 2, transformed with plasmid pTG44 was deposited on 6th Jun. 1986 under no. I 562.

The strain TGE901/pTG56 was deposited with the Collection Nationale de Culture de Microorganismes (National Collection of Microorganism Cultures), 25 rue du Docteur Roux, 75724 Paris, on 3rd Apr. 1987, under no. I.656.

BIBLIOGRAPHY

Capron, A. and Dessaint, J. P. (1985) Ann. Rev. Immunol. 3, 455–476

Balloul, J. M., Pierce, R. J./Grzych, J. M. and Capron, A. (1985) Mol. Biochem. Parasitol. 17, 105–114

Balloul, J. M., Grzych, J. M., Pierce, R. J. and Capron, A. (1986) submitted for publication Young, R. A. and Davis, R. W. (1983) Science 222, 778–782

Huynh, T. V. in DNA Cloning Techniques: A Practical Approach (Glover, D., Ed.) IRL Press, Oxford (1984)

Le Bouc, Y., Dreyer, D., Jaeger, F., Binoux, M. and Sondermeyer, P. (1986) FEBS Lett. 196, 108–112

Lathe, R. and Lecocq, J-P. (1977) Virology 83, 204–206

Hitzemann, R. A., Hagie, F. E., Hayflick, J. S., Chen, C. Y., Seeburg, P. H. and Derynck, R. (1982) Nucleic Ac. Res. 10, 7791–7808

Kieny, M. P., Lathe, R. and Lecocq, J-P. (1983) Gene 26, 91–99

Smith, G. L., Mackett, M. and Moss, B. (1983) Nature 302, 490–495

Panicalii, D. and Paoletti, E. (1982) Proc. Natl. Acad. Sci. USA 79, 4927–4931

Mackett, M., Smith, J. L. and Moss, B. (1982) Proc. Natl. Acad. Sci. USA 79, 7415–7419

Kieny, M. P., Lathe, R., Drillien, R., Spehner, D., Skory, S., Schmitt, D., Wiktor, T., Koprowski, H. and Lecocq, J-P. (1984) Nature 312, 163–166

Capron, M., Bazin, H., Torpier, G., Joseph, M. and Capron, A. (1981) J. Immunol. 126, 1764–1768

Habig, W. H., Pabst, M. J. and Jakoby, W. B. J. Biol. Chem. 249, 7130 (1974)

Moore, R. E., Davies, M. S., O'Connell, K. M., Harding, E. I., Wiegand, R. C. and Tiemeier, D. C. Nucl. Ac. Res. 14, 7227 (1986)

Smith, D. B., Davern, R. M., Board, P. G., Tiu, W. U., Garcia, E. G. and Mitchell, G. F. Proc. Natl. Acad. Sci. USA 83, 8703 (1986)

We claim:

1. A substantially purified protein having an amino acid sequence substantially as shown in FIGS. 1a–1c.

2. The protein according to claim 1, wherein said protein is recombinantly produced.

3. A substantially purified protein wherein said protein is recognized by antibodies raised against native p28 protein of *Schistosoma mansoni*.

4. A vaccine against schistosomiasis comprising the protein according to claim 1, together with a pharmaceutically acceptable carrier or adjuvant.

* * * * *